United States Patent
Lentz et al.

(10) Patent No.: US 8,481,555 B2
(45) Date of Patent: Jul. 9, 2013

(54) AZA-BICYCLIC AMINE N-OXIDE COMPOUNDS AS ALPHA-7 NICOTINIC ACETYLCHOLINE RECEPTOR LIGAND PRO-DRUGS

(75) Inventors: Kimberley A. Lentz, Durham, CT (US); Rex Denton, Madison, CT (US); James H. Cook, II, East Hampton, CT (US); Ivar M. McDonald, East Haddam, CT (US); Dalton King, Hamden, CT (US); Richard E. Olson, Orange, CT (US); Nenghui Wang, Guilford, CT (US); Robert A. Mate, Waterbury, CT (US); Christiana I. Iwuagwu, Hamden, CT (US); F. Christopher Zusi, Hamden, CT (US); John E. Macor, Guilford, CT (US); Matthew D. Hill, Wallingford, CT (US); Haiquan Fang, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 48 days.

(21) Appl. No.: 13/097,153

(22) Filed: Apr. 29, 2011

(65) Prior Publication Data

US 2012/0108596 A1 May 3, 2012

Related U.S. Application Data

(60) Provisional application No. 61/329,765, filed on Apr. 30, 2010.

(51) Int. Cl.
| | | |
|---|---|---|
| *A01N 43/42* | (2006.01) | |
| *A61K 31/44* | (2006.01) | |
| *C07D 491/10* | (2006.01) | |
| *C07D 491/20* | (2006.01) | |

(52) U.S. Cl.
USPC ............................................ 514/278; 546/19

(58) Field of Classification Search
None
See application file for complete search history.

(56) References Cited

U.S. PATENT DOCUMENTS

| | | | |
|---|---|---|---|
| 5,053,412 A | 10/1991 | Fisher et al. | |
| 7,863,291 B2 * | 1/2011 | Cook et al. | 514/305 |
| 2007/0004715 A1 | 1/2007 | Huang et al. | |
| 2010/0099684 A1 | 4/2010 | Cook, II et al. | |

FOREIGN PATENT DOCUMENTS

| | | |
|---|---|---|
| EP | 0 337 547 | 10/1989 |
| EP | 0 452 101 | 10/1991 |
| WO | WO 96/06098 | 2/1996 |
| WO | WO 03/092580 | 11/2003 |
| WO | WO 2005/005435 | 1/2005 |
| WO | WO 2006/065209 | 6/2006 |
| WO | WO 2008/000469 | 1/2008 |

OTHER PUBLICATIONS

U.S. Appl. No. 12/907,122, filed Oct. 19, 2010, McDonald et al.
U.S. Appl. No. 12/911,882, filed Oct. 26, 2010, McDonald et al.
Swain, C.J. et al., "Novel 5-HT$_3$ Antagonists: Indol-3-ylspiro(azabicycloalkane-3,5'(4'H)-oxazoles)", Journal of Medicinal Chemistry, vol. 35, No. 6, pp. 1019-1031 (1992).
Tatsumi, R. et al., "(R)-3'-(3-Methylbenzo[b]thiophen-5-yl)spiro[1-azabicyclo[2,2,2]octane-3,5'-oxazolidin]-2'-one, a Novel and Potent α7 Nicotinic Acetylcholine Receptor Partial Agonist Displays Cognitive Enhancing Properties", Journal of Medicinal Chemistry, vol. 49, No. 14, pp. 4374-4383 (2006).

* cited by examiner

*Primary Examiner* — Jeffrey Murray
(74) *Attorney, Agent, or Firm* — James Epperson

(57) ABSTRACT

The disclosure generally relates to compounds of the following formula, including their salts, as well as compositions and methods of using the compounds. The compounds are pro-drugs for ligands, agonists, and partial agonists for the nicotinic α7 receptor and may be useful for the treatment of various disorders of the central nervous system, especially affective and neurodegenerative disorders.

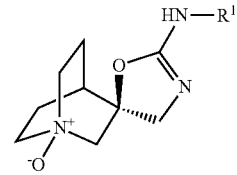

9 Claims, No Drawings

AZA-BICYCLIC AMINE N-OXIDE COMPOUNDS AS ALPHA-7 NICOTINIC ACETYLCHOLINE RECEPTOR LIGAND PRO-DRUGS

CROSS-REFERENCE TO RELATED APPLICATIONS

This patent application claims the benefit of U.S. provisional patent application No. 61/329,765 filed Apr. 30, 2010.

BACKGROUND OF THE INVENTION

This disclosure generally relates to compounds of formula I, including their salts, as well as compositions and methods of using the compounds. The compounds are prodrugs for ligands, agonists, and partial agonists for the nicotinic α7 receptor and may be useful for the treatment of various disorders of the central nervous system, especially affective and neurodegenerative disorders.

Schizophrenia is a serious mental disorder, affecting approximately 1% of the population. Its progressive course results in major impairment of mental and social functioning and often leads to the development of other pathologies. Susceptibility often runs in families, with both genetic and environmental factors thought to be important. The direct and indirect costs of the disease are estimated in the tens of billion dollars annually in the U.S. alone.

Patients with schizophrenia have an elevated risk of suicide (approximately a 10% lifetime risk). They have a 2.5 fold increase in all-cause mortality, resulting in a 20% lowered life expectancy. The onset of illness can result in cascade of unhealthy lifestyle factors and behaviors that elevate the risk of various conditions and consequently the risk of death.

The onset of schizophrenia is most often in late adolescence or early adulthood, and episodes recur throughout life. The disease is characterized by the expression of three distinct symptom domains: positive, negative and cognitive. Psychotic or positive symptoms include delusions, hallucinations, thought disorder and paranoia. Negative symptoms include negative affect, social withdrawal, and anhedonia. Cognitive dysfunction includes deficits in attention, working memory and executive function. The pathophysiology of schizophrenia is not well understood; however, most experts believe it is a multi-factorial disorder in which biological, genetic and environmental factors play a role. Most current therapies target the dopaminergic system and have resulted in the suggestion that an excess of dopaminergic neurotransmission underlies at least some aspects of schizophrenia. This theory received further support from findings that drugs which increase the levels of dopamine cause psychoses similar to the positive symptoms of the disease. Also, post mortem analysis of brains from schizophrenic patients indicate increased numbers of D2 dopamine receptors. Although newer antipsychotic agents, known as atypical antipsychotics, which are active at several additional neurotransmitter receptors, have been introduced in the past decade, these agents still share efficacy against the D2 dopamine receptor. All currently-used agents also have major limitations. Although positive symptoms are generally reduced in a majority of patients, these drugs do little to relieve the negative symptoms and cognitive deficits that are common and often most debilitating. In addition, antipsychotic agents have a number of unwanted and limiting side effects.

Nicotine is among the few agents which have a positive effect on cognitive function. Many schizophrenics smoke; the rate in patients is 2-4 times that of the general population, and up to 90% in schizophrenics who have been institutionalized do smoke. This smoking habit has been characterized as a form of self-medication.

Nicotinic acetylcholine receptors (nAChR's) are pentameric ligand-gated ion channels which are widely expressed through the central and peripheral nervous system. These channels are fast-desensitizing calcium channels which, when open, increase the intracellular concentration of the $Ca^{++}$ ion. Although there are 12 individual receptors, the most abundant nicotinic receptors in the brain are α4β2 and α7. The α4β2 complex has been identified as the "high affinity" nicotine site. The homo-pentameric α7 receptor selectively binds the natural product, α-bungarotoxin, which has allowed its relatively facile localization and measurement. The α7 receptor is primarily expressed in the cortex, hippocampus and subcortical limbic regions and commonly occurs pre-synaptically. The localization of α7 nAChRs in areas involved with learning and memory has led to studies using both knockout mice and pharmacological manipulation. It is involved in sensory gating, memory, and neuronal plasticity. Alpha7 agonists have been shown to increase the release of neurotransmitters in rodents, including dopamine, serotonin, glutamate and GABA. Compounds which selectively bind to the α7 receptor, such as α7 agonists and partial agonists, have been shown to improve learning and memory functions in normal and aged animals, reverse scopolamine-induced memory deficits, reverse deficits in cognition induced by NMDA antagonists, reverse pharmacologically-induced gating deficits, e.g. amphetamine induced gating disruption, and to possess some anxiolytic properties. The α7 agonists of the present invention are expected to be useful in the treatment of schizophrenia and cognitive disorders associated with schizophrenia.

Alzheimer's disease is a progressive neurodegenerative disorder, resulting in the general loss of cognitive functions. The incidence increases with age, to the degree that 25-50% of all individuals over 85 are estimated to suffer from some degree of dementia. A diagnosis of Alzheimer's implies that the remaining life expectancy is reduced by half, compared to normal adults.

Clinical signs of Alzheimer's disease are progressive cognitive deterioration, decreased ability to perform the activities of daily living and neuropsychiatric symptoms or behavioral changes. In the advanced stages of the disease, deterioration of musculature and mobility may lead to inability to feed oneself, and eventually to the patient becoming bedridden. Language becomes severely disorganized, and then is lost altogether. Patients are not able to perform even simple tasks independently and require constant supervision. The cost of institutional care makes up nearly 70% of the cost of the disease. Therefore, therapies which increase cognitive function and delay institutionalization are greatly needed.

Alzheimer's disease has been shown in several studies to be accompanied by a reduction in nicotinic receptors in the cortex and hippocampus. Nicotine injections or nicotine skin patches have been reported to significantly improve attention, memory and learning in Alzheimer's disease patients. While there is a progressive loss of nicotinic receptors during the course of Alzheimer's disease, the α7 neurons are relatively spared, compared to the more abundant α4 receptors. Recently, the administration of selective nicotinic α7 agonists has been shown to increase cognitive functioning in Alzheimer's patients when dosed as long as 8 weeks. This clinical data is consistent with pre-clinical data showing α7 agonists and partial agonists improve learning and memory functions in normal and aged animals and reverse scopolamine-induced memory deficits. Thus, the compounds of the present invention may be useful in the treatment and prevention of Alzheimer's disease. The amyloid peptide Aβ42 has been shown to bind to the α7 nicotinic receptor (Wang et al., J. Biol. Chem., 2000, 275:5626-5632; J. Neurochem. 2000, 75:1155-1161). This association may facilitate the aggregation of Aβ42, believed to be important in the toxic effects of Aβ42, and may also cause disregulation of signaling through α7 nicotinic receptors. Deletion of the α7 receptor gene improves cognitive deficits and synaptic pathology in a mouse model of Alzheimer's disease (Dziewczapolski et al., J. Neuroscience, 2009, pp 8805-8815). The compounds of the present invention may disrupt the interaction of Aβ42 and α7 receptors. Treatment with α7 agonists and partial agonists may represent an approach for disease modification in Alzheimer's disease. Alpha7 receptors may also mediate inflammatory processes in neurodegenerative conditions, such as Alzheimer's disease (Conejero-Goldberg et al., Neurosci. and Biobehav. Rev., 2008, 32, pp 693-706). The α7 agonists and partial agonists of the present invention may be useful in reducing inflammation in neurodegenerative diseases and disorders, such as Alzheimer's disease.

The α7 receptor has also been shown to be involved in the reduction of inflammation via the vagus nerve. In addition, the α7 receptor is expressed in synoviocytes from RA and OA patients, and α7 agonists have been shown to inhibit the proinflammatory cascade that occurs in the rheumatoid joint (Waldberger et al., Arthritis and Rheumatism, Vol 58, pp 3439-3449). Thus, the compounds of the present invention may be useful in the treatment of inflammatory conditions, such as rheumatoid arthritis and osteoarthritis.

Nicotinic receptors containing the α7 subunit are present on mucosal mast cells known to be involved in gastrointestinal hypersensitivity (Kageyama-Yahara et al., Biochem and Biophys. Research Commun., 2008, v. 377, pp 321-325). The α7 agonist GTS-21 inhibits the antigen-induced degranulation of mucosal mast cells, suggesting that α7 agonists may be useful in the treatment of hypersensitive bowel conditions, such as ulcerative colitis.

In a recent report (Marrero et al., JPET Fast Forward, Sep. 28, 2009, DOI: 10.1124/jpet.109.154633), an α7 agonist was shown to decrease weight gain and food intake and reduce the elevated plasma levels of triglycerides, glucose, glycated hemoglobin and TNFα in a mouse model of type II diabetes (db/db mice which are deficit in leptin receptors). The α7 agonists and partial agonists of the present invention may be useful in the treatment of diabetes.

The following references provide general reviews of the nicotinic receptor system and α7 receptors and ligands: Picciotto and Zoli, J. Neurobio. (2002) 53:641-655; Brening, et al, Ann. Reports in Med. Chem. (2005) 40:3-16; Dani and Bertrand, Ann. Rev. Pharm. Tox. (2007) 47:699-729; Olincy and Stevens, Biochem. Pharmacol. (2007) 74:1192-1201; Broad, et al, Drugs Future (2007) 32 (2):161-70; de Jonge and Ulloa, Brit. J. Pharmacol. (2007) 151:915-929; Romanelli, et al, ChemMedChem (2007) 2(6):746-767; Lightfoot et al., Progress in Medicinal Chemistry (2008), v 46, pp 131-171; Concotta et al., Current Opinion in Investigational Drugs (2008), v 9, pp 47-56; Leiser et al., Pharmacol. and Therapeutics (2009), doi:10:1016/j.pharmthera.2009.03.009).

Ligands for the nicotinic α7 receptor have been disclosed. See: U.S. Pat. No. 7,863,291 and US 20100099684.

The invention provides technical advantages, for example, the compounds are novel and are prodrugs for ligands for the nicotinic α7 receptor and may be useful for the treatment of various disorders of the central nervous system, especially affective and neurodegenerative disorders. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of formula I, including pharmaceutically acceptable salts, and compositions and methods of treatment using these compounds. The compounds may be useful for the treatment of various disorders of the central nervous system.

One aspect of the invention is a compound of formula I, or a stereoisomer thereof,

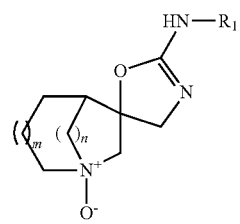

wherein:
m is 0 or 1;
n is 1 or 2;
$R^1$ is selected from the group consisting of isoxazolyl, pyrazolyl, oxazolyl, thiazolyl, imidazolyl, oxadiazolyl, thiadiazolyl, triazolyl, pyridinyl, pyrazinyl, pyridazinyl, pyrimidinyl, triazinyl, quinolinyl, isoquinolinyl, tetrahydroisoquinolinyl, quinoxalinyl, quinazolinyl, naphthyridinyl, indazolyl, indolyl, 2-indolonyl, benzisoxazolyl, benzoisothiazolyl, benzoxazolyl, benzothiazolyl, benzimidazolyl, furopyridinyl, thienopyridinyl, thienopyrimidinyl, isothiazolopyridinyl, thiazolopyridinyl, thiazolopyridinonyl, thiazolopyrazinyl, thiazolopyrimidinyl, triazolopyridinyl, triazolopyrazinyl, pyrrolotriazinyl, 5,6-dihydrobenzo[h]quinazolinyl, 5H-chromeno[4,3-d]pyrimidinyl, 6,7-dihydro-5H-cyclopenta[d]pyrimidinyl, 5,6,7,8-tetrahydroquinazolinyl, 7,8-dihydroquinazolin-5(6H)-onyl, tetrahydrobenzothiazolyl, imidazothiazolyl, oxazolopyridinyl, triazolopyridazinyl, triazolopyrimidinyl, imidazolopyridazinyl, imidazopyrazinyl, imidazopyridinyl, pyrrolopyrazinyl, benzotriazolyl, pyrrolopyrimidinyl, purinyl, pyrrolopyridinyl, and benzotriazinyl and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, nitro, $C_{1-4}$alkylsulfonyl, $NR^2R^3$, pyrrolidinonyl, methylenedioxy, furyl, thienyl, pyrazolyl, imidazolyl, pyrrolyl, oxadiazolyl, thiazolyl, triazolyl, pyrazinyl, pyrimidinyl, naphthyl, $C_{1-4}$alkylamido, $CONR^2R^3$, pyridyl, phenyl, and benzyl, and where imidazolyl, pyridyl, phenyl, pyrrolyl, oxadiazolyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, phenyl, benzyl, pyridylmethyl and $NR^2R^3$;
$R^2$ is hydrogen, phenyl, $C_{1-4}$alkyl, $C_{1-4}$hydroxyalkyl, or $C_{1-4}$-aminoalkyl;
$R^3$ is hydrogen, $C_{1-4}$alkyl, $C_{1-4}$hydroxyalkyl, or $C_{1-4}$-aminoalkyl;
or $R_2$ and $R_3$ taken together with the nitrogen atom to which they are attached is azetidinyl, pyrrolidinyl, piperidinyl, piperazinyl, N—($C_{1-4}$alkyl)piperazinyl, morpholinyl, or homopiperidinyl;
or a pharmaceutically acceptable salt thereof.

Another aspect of the invention is a compound of formula I

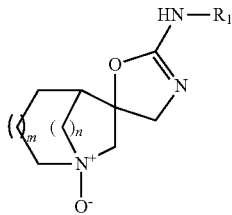

wherein:
m is 0 or 1;
n is 1 or 2;
$R^1$ is selected from the group consisting of isoxazolyl, pyrazolyl, oxazolyl, thiazolyl, imidazolyl, oxadiazolyl, thiadiazolyl, triazolyl, pyridinyl, pyrazinyl, pyridazinyl, pyrimidinyl, triazinyl, quinolinyl, isoquinolinyl, tetrahydroisoquinolinyl, quinoxalinyl, quinazolinyl, naphthyridinyl, indazolyl, indolyl, 2-indolonyl, benzisoxazolyl, benzoisothiazolyl, benzoxazolyl, benzothiazolyl, benzimidazolyl, furopyridinyl, thienopyridinyl, thienopyrimidinyl, isothiazolopyridinyl, thiazolopyridinyl, thiazolopyridinonyl, thiazolopyrazinyl, thiazolopyrimidinyl, triazolopyridinyl, triazolopyrazinyl, pyrrolotriazinyl, 5,6-dihydrobenzo[h]quinazolinyl, 5H-chromeno[4,3-d]pyrimidinyl, 6,7-dihydro-5H-cyclopenta[d]pyrimidinyl, 5,6,7,8-tetrahydroquinazolinyl, 7,8-dihydroquinazolin-5(6H)-onyl, and tetrahydrobenzothiazolyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, nitro, $C_{1-4}$alkylsulfonyl, $NR^2R^3$, pyrrolidinonyl, methylenedioxy, furyl, thienyl, pyrazolyl, imidazolyl, thiazolyl, triazolyl, pyrazinyl, pyrimidinyl, naphthyl, $C_{1-4}$alkylamido, $CONR^2R^3$, pyridyl, phenyl, and benzyl, and where imidazolyl, pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^2R^3$;
$R^2$ is hydrogen, $C_{1-4}$alkyl, $C_{1-4}$hydroxyalkyl, or $C_{1-4}$-aminoalkyl;
$R^3$ is hydrogen, $C_{1-4}$alkyl, $C_{1-4}$hydroxyalkyl, or $C_{1-4}$-aminoalkyl;
or $R_2$ and $R_3$ taken together with the nitrogen atom to which they are attached is azetidinyl, pyrrolidinyl, piperidinyl, piperazinyl, N—($C_{1-4}$alkyl)piperazinyl, morpholinyl, or homopiperidinyl;
or a pharmaceutically acceptable salt thereof.

Another aspect of the invention is a stereoisomer of formula I according to formula Ia.

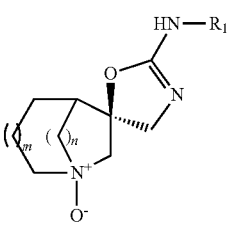

Another aspect of the invention is a compound of formula I or Ia where $R^1$ is selected from the group consisting of dimethylisoxazolyl, (methyl)(phenyl)isoxazolyl, methylpyrazolyl, dimethylpyrazolyl, thienylpyrazolyl, methoxyphenylpyrazolyl, thiazolyl, bromothiazolyl, cyanothiazolyl, methylthiazolyl, dimethylthiazolyl, (methyl)(phenyl)thiazolyl, isopropylthiazolyl, butylthiazolyl, benzylthiazolyl, methoxyphenylmethylthiazolyl, phenylthiazolyl, chlorophenylthiazolyl, methoxyphenylthiazolyl, (methoxyphenyl)(methyl)thiazolyl, pyridinylthiazolyl, (phenyl)(methyl)imidazolyl, methyloxadiazolyl, ethyloxadiazolyl, methylthiadiazolyl, fluorophenylthiadiazolyl, furylthiadiazolyl, (dimethylcarboxamido)(methyl)thiazolyl, (pyrrolidinylCO)thiazolyl, phenyltriazolyl, pyridinyl, bromopyridinyl, chloropyridinyl, (chloro)(fluoro)pyridinyl, (chloro)(methyl)pyridinyl, dichloropyridinyl, fluoropyridinyl, cyanopyridinyl, (cyano)(methyl)pyridinyl, (cyano)(dimethyl)pyridinyl, methoxypyridinyl, (methylpyrrolidinyl)pyridinyl, phenylpyridinyl, methoxypyridinylpyridinyl, pyridazinyl, bromopyridazinyl, chloropyridazinyl, methylpyridazinyl, methoxypyridazinyl, methylthiopyridazinyl, pyrrolidinylpyridazinyl, pyrrolidinonylpyridazinyl, phenylpyridazinyl, pyridinylpyridazinyl, methoxypyridinylpyridazinyl, pyrimidinyl, (bromo)(isopropyl)pyrimidinyl, (bromo)(dimethyl)pyrimidinyl, (bromo)(cyclopropyl)pyrimidinyl, (bromo)(methoxy)pyrimidinyl, (bromo)(phenyl)pyrimidinyl, (bromo)(pyridinyl)pyrimidinyl, chloropyrimidinyl, (chloro)(dimethyl)pyrimidinyl, (methyl)(methoxy)pyrimidinyl, methylpyrimidinyl, ethylpyrimidinyl, (methyl)(phenyl)pyrimidinyl, dimethylpyrimidinyl, butylpyrimidinyl, isopropylpyrimidinyl, cyclopropylpyrimidinyl, methoxypyrimidinyl, dimethoxypyrimidinyl, isopropoxypyrimidinyl, cyclopentoxypyrimidinyl, difluoromethoxypyrimidinyl, trifluoroethoxypyrimidinyl, phenoxypyrimidinyl, methylthiopyrimidinyl, phenylpyrimidinyl, chlorophenylpyrimidinyl, methylphenylpyrimidinyl, methoxyphenylpyrimidinyl, (phenyl)(triazolyl)pyrimidinyl, pyridinylpyrimidinyl, methoxypyridinylpyrimidinyl, methoxypyrimidinylpyrimidinyl, naphthylpyrimidinyl, pyrazinyl, bromopyrazinyl, (bromo)(methoxy)pyrazinyl, chloropyrazinyl, methylpyrazinyl, dimethylpyrazinyl, butylpyrazinyl, cyanopyrazinyl, methoxypyrazinyl, isopropoxypyrazinyl, trifluoromethylpyrazinyl, and phenylpyrazinyl, and dimethyltriazinyl; or a pharmaceutically acceptable salt thereof.

Another aspect of the invention is a compound of formula I or Ia where $R^1$ is selected from the group consisting of dimethylpyridinoisoxazolyl, benzoxazolyl, chlorobenzoxazolyl, fluorophenylbenzoxazolyl, ethylphenylbenzoxazolyl, dimethylaminophenylbenzoxazolyl, pyridinylbenzoxazolyl, benzothiazolyl, acetamidobenzothiazolyl, bromobenzothiazolyl, chlorobenzothiazolyl, (chloro)(methyl)benzothiazolyl, (chloro)(methoxy)benzothiazolyl, fluorobenzothiazolyl, difluorobenzothiazolyl, cyanobenzothiazolyl, methylbenzothiazolyl, dimethylbenzothiazolyl, (methyl)(methoxy)benzothiazolyl, ethylbenzothiazolyl, trifluoromethylbenzothiazolyl, hydroxybenzothiazolyl, methoxybenzothiazolyl, ethoxybenzothiazolyl, isopropoxybenzothiazolyl, trifluoromethoxybenzothiazolyl, difluoromethoxybenzothiazolyl, dimethoxybenzothiazolyl, morpholinylbenzothiazolyl, (pyrrolidinylCO)benzothiazolyl, methylsulfonylbenzothiazolyl, chlorothiazolopyridinyl, dimethylthiazolopyridinyl, benzyloxythiazolopyridinyl, difluoromethoxythiazolopyridinyl, benzotriazolyl, indolonyl, indazolyl, bromoindazolyl, chloroindazolyl, fluoroindazolyl, (methyl)(methoxy)indazolyl, methoxyindazolyl, trifluoromethylindazolyl, trifluoromethoxyindazolyl, difluoromethoxyindazolyl, benzimidazolyl, fluorobenzimidazolyl, methylbenzimidazolyl, (methyl)(methoxy)benzimidazolyl, methoxybenzimidazolyl, tetrahydrobenzothiazolyl, furopyridinyl, dimethylfuropyrimidinyl, thienopyrimidinyl, isopropylthienopyrimidinyl, dimethylthienopyrimidinyl, chlorotriazolopyridinyl, methyltriazolopyridinyl, trifluoromethyltriazolopyridinyl, methoxytriazolopyridinyl, triazolopyrazinyl, bromopyrrolotriazinyl, dimethylaminothiazolopyrimidinyl, thiazolopyazinyl, bromothiazolopyazinyl, methoxythiazolopyazinyl, methylthiothiazolopyazinyl, methoxythiazolopyrimidinyl, (methyl)(methoxy)thiazolopyrimidinyl, quinolinyl, bromoquinolinyl, fluoroquinolinyl, methylquinolinyl, (methyl)(methoxy)quinolinyl, isoquinolinyl, bromoisoquinolinyl, dichloroisoquinolinyl, methylisoquinolinyl, dimethylisoquinolinyl, quinoxalinyl, chloroquinoxalinyl, methylquinoxalinyl, methoxyquinoxalinyl, quinazolinyl, bromoquinazolinyl, naphthyridinyl, 5,6-dihydrobenzo[h]quinazolinyl, 5H-chromeno[4,3-d]pyrimidinyl, 6,7-dihydro-5H-cyclopenta[d]pyrimidinyl, 5,6,7,8-tetrahydroquinazolinyl, and 7,8-dihydroquinazolin-5(6H)-onyl; or a pharmaceutically acceptable salt thereof.

Another aspect of the invention is a compound of formula I or Ia where $R^1$ is selected from the group consisting of phenylthiazolyl, (chloro)(methyl)pyridinyl, (bromo)(phenyl)pyrimidinyl, methoxypyrimidinyl, difluoromethoxypyrimidinyl, difluoroethoxypyrimidinyl, cyclopentoxypyrimidinyl, (methylphenyl)pyrimidinyl, (methoxyphenyl)pyrimidinyl, bromopyrazinyl, chloropyrazinyl, methylthiopyrazinyl, methoxybenzothiazolyl, ethoxybenzothiazolyl, difluoromethoxybenzothiazolyl, thiazolopyridinonyl, trifluoromethylindazolyl, benzimidazolyl, isoquinoinyl, and quinazolinyl or a pharmaceutically acceptable salt thereof.

Another aspect of the invention is a compound or formula I or Ia where $R^1$ is selected from the group consisting of bromopyridinyl, dichloropyridinyl, methoxypyridinyl, (pyridinyl)pyridinyl, (phenyl)pyrimidinyl, (methoxypyridinyl)pyrimidinyl, (pyrazolyl)pyrimidinyl, chloropyrazinyl, (bromo)(chloro)pyrazinyl, and chlorobenzothiazolyl; or a pharmaceutically acceptable salt thereof.

Another aspect of the invention is a compound or formula I or Ia where $R^1$ is selected from the group consisting of thiazolyl, pyridinyl, pyridazinyl, pyrimidinyl, pyrazinyl, benzothiazolyl, thiazolopyridinyl, indazolyl, benzimidazolyl, isoquinolinyl, and quinazolinyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, $C_{1-4}$alkylsulfonyl, $NR^2R^3$, pyrrolidinonyl, methylenedioxy, furyl, thienyl, triazolyl, pyrimidinyl, naphthyl, $C_{1-4}$alkylamido, $CONR^2R^3$, pyridyl, phenyl, and benzyl, and where pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^2R^3$; or a pharmaceutically acceptable salt thereof.

Another aspect of the invention is a compound or formula I or Ia where $R^1$ is selected from the group consisting of pyridinyl, pyrimidinyl, pyrazinyl, thiazolopyridinyl, and isoquinolinyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, $C_{1-4}$alkylsulfonyl, $NR^2R^3$, pyrrolidinonyl, methylenedioxy, furyl, thienyl, triazolyl, pyrimidinyl, $C_{1-4}$alkylamido, $CONR^2R^3$, pyridyl, phenyl, and benzyl, and where pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^2R^3$; or a pharmaceutically acceptable salt thereof.

Another aspect of the invention is a compound or formula I or Ia where $R^1$ is selected from the group consisting of pyridinyl and isoquinolinyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, $C_{1-4}$alkylsulfonyl, $NR^2R^3$, pyrrolidinonyl, methylenedioxy, furyl, thienyl, triazolyl, pyrimidinyl, naphthyl, $C_{1-4}$alkylamido, $CONR^2R^3$, pyridyl, phenyl, and benzyl, and where pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^2R^3$; or a pharmaceutically acceptable salt thereof.

Another aspect of the invention is a compound or formula I or Ia where $R^1$ is selected from the group consisting of thiazolyl, pyridinyl, pyrazinyl, pyrimidinyl, isoquinolinyl, or quinoxalinyl, and is substituted with 0-2 substituents selected from the group consisting of halo; alkyl; alkoxy; cycloalkoxy; pyrazolyl; imidazolyl; pyridinyl substituted with 0-2 halo, alkyl, or alkoxy substituents; and phenyl substituted with 0-2 halo, alkyl, or alkoxy substituents; or a pharmaceutically acceptable salt thereof.

Another aspect of the invention is a compound or formula I or Ia where $R^1$ is selected from the group consisting of (phenyl)thiazolyl, (fluoro)(bromo)pyridinyl, (chloro)(methyl)pyridinyl, chloropyrazinyl, (fluoropyridinyl)pyridinyl, (bromo)(phenyl)pyrimidinyl, (cyclopentoxy)pyrimidinyl, (imidazolyl)pyrimidinyl, ((methyl)phenyl)pyrimidinyl, isoquinolinyl, fluoroisoquinolinyl, or quinoxalinyl, or a pharmaceutically acceptable salt thereof.

Another aspect of the invention is a compound or formula I or Ia where $R^1$ is selected from the group consisting of bromopyridinyl, dichloropyridinyl, (pyridinyl)pyridinyl, (pyrazolyl)pyrimidinyl, methoxypyrimidinyl, (methoxypyridinyl)pyrimidinyl, (phenyl)pyrimidinyl, or bromomchloropyrazinyl, or a pharmaceutically acceptable salt thereof.

Another aspect of the invention is a compound of formula I where $R_1$ is selected from the group consisting of thiazole, thiadiazole, isoxazole, oxazole, pyrazole, imidazole, pyridine, pyrazine, pyridazine, pyrimidine, quinoline, isoquinoline, quinoxaline, indazole, indole, 2-indolone, benzothiazole, benzimidazole, benzoxazole, benzo[d]isothiazole, benzisoxazole, isothiazolo-[5,4-b]pyridine, (1,2,4)-triazolo[1,5-a]pyridine, thiazolo[5,4-b]pyridine and tetrahydrobenzothiazole in which each group is optionally substituted with one or two substituents selected from the group consisting of $C_{1-4}$alkyl, $C_{1-4}$alkoxy, halogen, hydroxy, cyano, trifluoromethyl, difluoromethyl, fluoromethyl, trifluoromethoxy, difluoromethoxy, $C_{1-4}$alkylsulfonyl, furyl, morpholino, methylenedioxy, pyridyl, $C_{1-4}$alkylphenyl, halophenyl, dimethylaminophenyl, $C_{1-4}$alkylamido, —$CONR_2R_3$ in which $R_2$ and $R_3$ each are independently hydrogen, $C_{1-4}$alkyl, hydroxy $C_{1-4}$alkyl, amino $C_{1-4}$alkyl or $R_2$ and $R_3$ taken together with the atom to which they are attached are $C_{3-6}$cycloalkyl; phenyl, substituted phenyl, phenylmethyl, substituted phenylmethyl in which said substituted phenyl and substituted phenylmethyl are substituted with substituents independently selected from the group consisting of halogen, $C_{1-4}$alkyl, $C_{1-4}$alkoxy, trifluoromethyl and trifluoromethoxy; or a pharmaceutically acceptable salt thereof.

Another aspect of the invention is a compound of formula I according to the following structure:

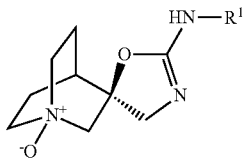

Another aspect of the invention is a compound of formula I according to the following structure:

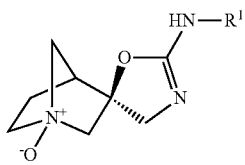

Another aspect of the invention is a compound of formula I according to the following structure:

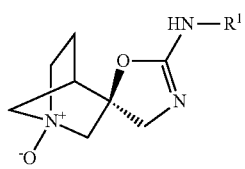

Another aspect of the invention is a compound of formula I according to the following structure:

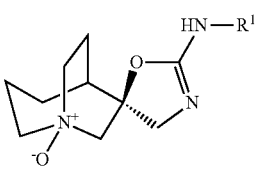

Another aspect of the invention is a compound of formula I according to the following structure:

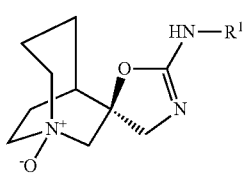

Another aspect of the invention is a compound of formula I according to the following structure:

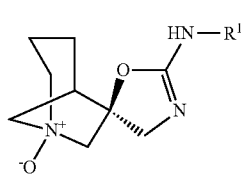

Another aspect of the invention is a compound of formula I according to the following structure:

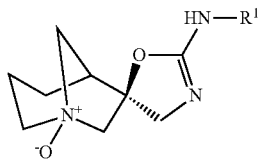

For a compound of formula I or Ia, the scope of any instance of a variable substituent, including $R^1$, $R^2$, and $R^3$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 4 carbons. "Alkenyl" means a straight or branched alkyl group composed of 2 to 4 carbons with at least one double bond. "Alkynyl" means a straight or branched alkyl group composed of 2 to 4 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

The substituents described above may be attached at any suitable point of attachment unless otherwise specified. However, it is understood that the compounds encompassed by the present invention are those that are chemically stable as understood by those skilled in the art. Additionally, the compounds encompassed by the present disclosure are those that are suitably stable for use as a pharmaceutical agent.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinafoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art.

The invention includes all tautomeric forms of the compounds. An example of a tautomeric pair is shown below.

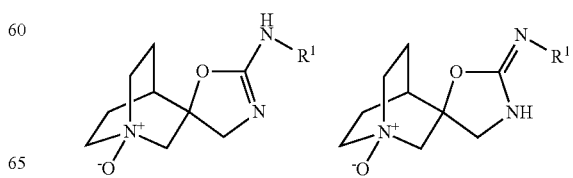

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Some of the compounds may be prepared using the reactions and techniques described in this section. The reactions are performed in solvents appropriate to the reagents and materials employed and are suitable for the transformations being effected. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Abbreviations used in the description generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

$^1$H-NMR spectra were run on a Bruker 500, 400, or 300 MHz instrument and chemical shifts were reported in ppm (δ) with reference to tetramethylsilane (δ=0.0). All evaporations were carried out under reduced pressure. Unless otherwise stated, LC/MS analyses were carried out on a Shimadzu instrument using a Phenomenex-Luna 4.6×50 mm S 10 reverse phase column employing a flow rate of 4 mL/min using a 0.1% TFA in methanol/water gradient [0-100% in 3 min, with 4 min run time] and a UV detector set at 220 nm or Gemini C18 4.6×50 mm 5 u reverse phase column employing a flow rate of 5 mL/min using a 10 mM ammonium acetate acetonitrile/water gradient [5-95% in 3 min, with 4 min run time] and a UV detector set at 220 nm (negative-ion mass spectrometry). Unless otherwise stated, purification could be done by preparative C-18 column employing gradients of methanol-water containing 0.1% of trifluoroacetic acid (TFA), and using a Shimadzu High Performance Liquid Preparative Chromatographic System employing an XTERRA 30×100 mm S5 column at 40 mL/min flow rate with a 12 min gradient.

Some of the compounds of the instant invention may be prepared by oxidizing the free base of the nicotinic α7 ligand to the N-oxide using a suitable oxidizing agent, for example 3-chlorobenzoperoxoic acid:

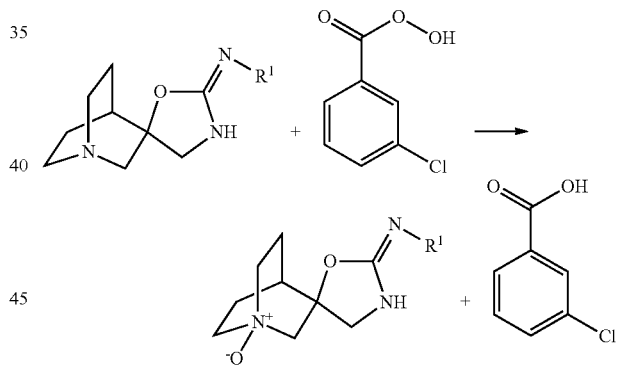

The oxidizing agent "oxone" (potassium mono-persulfate) may also be used.

EXAMPLE 1

(S)-2-(Isoquinolin-3-ylamino)-4H-1'-azaspiro[oxazole-5,3'-bicyclo[2.2.2]octane]1'-oxide

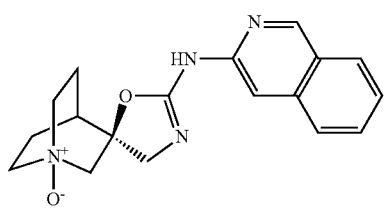 [SMILES: [O-][N+]12CCC(CC1)[C@]1(CN=C(Nc3cc4ccccc4cn3)O1)C2]

A solution of (R)—N-(isoquinolin-3-yl)-4H-1'-azaspiro[oxazole-5,3'-bicyclo[2.2.2]octan]-2-amine (771 mg, 2.5 mmol) (designated Compound A) and 3-chlorobenzoperoxoic acid (518 mg, 3.00 mmol) in THF (12.5 mL) was stirred at room temperature for 3.5 h. The reaction was concentrated and the crude product was purified by flash chromatography on a 160 g silica gel cartridge with 5 to 15% [9:1 MeOH/NH4OH] in EtOAc. Pure fractions were pooled, concentrated and dried. The residue was dissolved in 5 mL water and eluted on a Waters Oasis HLB 35 cc (6 g) LP extraction cartridge with 500 mL water, followed by MeOH to elute the pure product (S)-2-(isoquinolin-3-ylamino)-4H-1'-azaspiro[oxazole-5,3'-bicyclo[2.2.2]octane]1'-oxide (designated as compound B) (695 mg, 86% yield).

1H NMR (400 MHz, MeOD) δ ppm 8.96 (1H, s), 7.87 (1H, d, J=8.31 Hz), 7.67 (1H, d, J=8.56 Hz), 7.55 (1H, ddd, J=8.25, 6.99, 1.13 Hz), 7.47 (1H, s), 7.37 (1H, td, J=7.55, 1.01 Hz), 3.92 (1H, d, J=10.83 Hz), 3.78 (1H, d, J=10.83 Hz), 3.58-3.72 (2H, m), 3.37-3.47 (3H, m), 3.19-3.30 (1H, m), 2.38 (1H, td, J=6.67, 3.53 Hz), 2.18 (1H, br. s.), 1.93-2.10 (3H, m). LCMS: RT=0.55 min, MH+=325.2 [ Waters Acquity SDS: 2 to 98% B, 1 min gradient; hold 98% B, 0.5 min; flow rate 0.8 mL/min; Solvent A: 100% H2O/0.05% TFA; Solvent B: 100% ACN/0.05% TFA].

EXAMPLE 2

(S)-2-(Quinoxalin-2-ylamino)-4H-1'-azaspiro[oxazole-5,3'-bicyclo[2.2.2]octane]1'-oxide

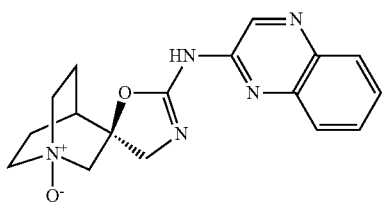 [SMILES: [O-][N+]12CCC(CC1)[C@]1(CN=C(Nc3cnc4ccccc4n3)O1)C2]

A solution of (R)—N-(quinoxalin-2-yl)-4H-1'-azaspiro[oxazole-5,3'-bicyclo[2.2.2]octan]-2-amine (190 mg, 0.614 mmol) and 3-chlorobenzoperoxoic acid (165 mg, 0.737 mmol) in 4 mL THF was stirred at room temperature for 2 h. The reaction was concentrated and the crude product was purified by flash chromatography on a 40 g silica gel cartridge with 1 to 30% [9:1 MeOH/NH4OH] in EtOAc. Pure fractions were pooled, concentrated, redissolved in CHCl3, and filtered through a 0.45 u filter to yield (S)-2-(quinoxalin-2-ylamino)-4H-1'-azaspiro[oxazole-5,3'-bicyclo[2.2.2]octane]1'-oxide (192 mg, 96% yield). 1H NMR (400 MHz, CHLOROFORM-d) δ ppm 9.89 (1H, br. s.), 8.58 (1H, s), 7.93 (1H, dd, J=8.31, 1.26 Hz), 7.70 (1H, dd, J=8.31, 1.01 Hz), 7.60 (1H, ddd, J=8.25, 6.99, 1.38 Hz), 7.50 (1H, ddd, J=8.25, 6.99, 1.38 Hz), 4.01 (1H, d, J=10.07 Hz), 3.84 (1H, d, J=9.82 Hz), 3.78-3.83 (1H, m), 3.64 (1H, dd, J=14.35, 2.27 Hz), 3.26-3.58 (4H, m), 2.50-2.65 (1H, m), 2.27 (1H, br. s.), 2.06-2.19 (1H, m, J=14.26, 10.42, 4.15, 4.15 Hz), 1.88-2.03 (2H, m). LCMS: RT=0.72 min, MH+=326.1 [ Waters Acquity SDS: 2 to 98% B, 1 min gradient; hold 98% B, 0.5 min; flow rate 0.8 mL/min; Solvent A: 100% H2O/0.05% TFA; Solvent B: 100% ACN/0.05% TFA]. LCMS: RT=1.15 min, MH-=324.2, MH+=326.2 [ Phenomenex LUNA C18 3 m (2.0×30 mm); 0 to 100% B, 2 min gradient; flow rate 1 mL/min; Solvent A: 5% MeOH: 95% water: 10 mM NH4OAc; Solvent B: 95% MeOH: 5% water: 10 mM NH4OAc; 220 nM].

EXAMPLE 3

(R)-2-(Isoquinolin-3-ylamino)-4H-1'-azaspiro[oxazole-5,3'-bicyclo[2.2.2]octane]1'-oxide

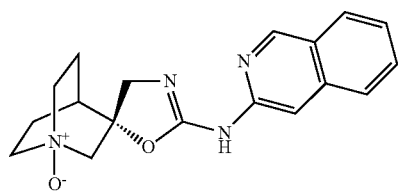 [SMILES: [O-][N+]12CCC(CC1)[C@@]1(CN=C(Nc3cc4ccccc4cn3)O1)C2]

By a method similar to that used in Example 1, (S)—N-(isoquinolin-3-yl)-4H-1'-azaspiro[oxazole-5,3'-bicyclo[2.2.2]octan]-2-amine (108 mg, 0.350 mmol) and 3-chlorobenzoperoxoic acid (72.5 mg, 0.420 mmol) gave (R)-2-(isoquinolin-3-ylamino)-4H-1'-azaspiro[oxazole-5,3'-bicyclo[2.2.2]octane]1'-oxide (95 mg, 83% yield). 1H NMR (500 MHz, MeOD) δ ppm 9.04 (1H, s), 7.97 (1H, d, J=8.24 Hz), 7.76 (1H, d, J=8.24 Hz), 7.61-7.67 (1H, m), 7.44-7.49 (2H, m), 4.03 (1H, d, J=10.99 Hz), 3.87 (1H, d, J=10.99 Hz), 3.65-3.77 (2H, m), 3.44-3.53 (3H, m), 3.27-3.31 (1H, m), 2.43-2.55 (1H, m), 2.32 (1H, br. s.), 2.04-2.22 (3H, m). LCMS: RT=0.54 min, MH+=325.2 [ Waters Acquity SDS: 2 to 98% B, 1 min gradient; hold 98% B, 0.5 min; flow rate 0.8 mL/min; Solvent A: 100% H2O/0.05% TFA; Solvent B: 100% ACN/0.05% TFA].

EXAMPLE 4

(S)-2-(5-m-Tolylpyrimidin-2-ylamino)-4H-1'-azaspiro[oxazole-5,3'-bicyclo[2.2.2]octane]1'-oxide

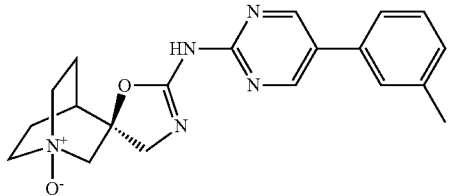 [SMILES: Cc1cccc(-c2cnc(NC3=NC[C@@]4(C[N+]5([O-])CCC4CC5)O3)nc2)c1]

mCPBA (0.074 g, 0.332 mmol) was added to a suspension of (R)—N-(5-m-tolylpyrimidin-2-yl)-4H-1'-azaspiro[oxazole-5,3'-bicyclo[2.2.2]octan]-2-amine (0.116 g, 0.332 mmol) in THF (10 ml). The mixture was stirred at room temperature for 18 h, concentrated and purified by silica gel chromatography (5-25% 9:1 methanol:ammonium hydroxide-ethyl acetate) to afford (S)-2-(5-m-tolylpyrimidin-2-ylamino)-4H-1'-azaspiro[oxazole-5,3'-bicyclo[2.2.2]octane]1'-oxide as an off-white solid (0.067 g, 0.176 mmol, 53%). 1H NMR (400 MHz, MeOD) δ ppm 8.79 (2H, s), 7.27-7.49 (3H, m), 7.20 (1H, d, J=7.55 Hz), 4.03 (1H, d, J=10.32 Hz), 3.88 (1H, d, J=10.58 Hz), 3.59-3.77 (2H, m), 3.38-3.52 (3H, m), 3.21-3.28 (1H, m), 2.40-2.52 (1H, m), 2.28-2.35 (1H, m), 1.96-2.21 (3H, m). LC/MS RT=1.71; [M+H]+=366.34.

EXAMPLE 5

(S)-2-(6-(Cyclopentyloxy)pyrimidin-4-ylamino)-4H-1'-azaspiro[oxazole-5,3'-bicyclo[2.2.2]octane]1'-oxide

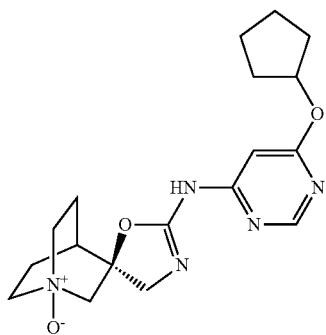 [SMILES: [O-][N+]12CCC(CC1)[C@]1(CN=C(Nc3cc(OC4CCCC4)ncn3)O1)C2]

mCPBA (0.114 g, 0.510 mmol) was added to a solution of (R)—N-(6-(cyclopentyloxy)pyrimidin-4-yl)-4H-1'-azaspiro[oxazole-5,3'-bicyclo[2.2.2]octan]-2-amine (0.175 g, 0.510 mmol) in THF (15 ml). The mixture was stirred at room temperature for 18 h and concentrated. The residue was purified by silica gel chromatography (5-25% 9:1 methanol:ammonium hydroxide-ethyl acetate) to afford (S)-2-(6-(cyclopentyloxy)pyrimidin-4-ylamino)-4H-1'-azaspiro[oxazole-5,3'-bicyclo[2.2.2]octane]1'-oxide an off-white solid (0.076 g, 0.207 mmol, 41%). $^1$H NMR (400 MHz, MeOD) δ ppm 8.38 (1H, s), 6.34 (1H, br. s.), 5.18-5.37 (1H, m), 4.01 (1H, d, J=11.08 Hz), 3.85 (1H, d, J=10.83 Hz), 3.58-3.75 (2H, m), 3.34-3.53 (3H, m), 3.20-3.27 (1H, m), 2.32-2.46 (1H, m), 2.23-2.31 (1H, m), 1.98-2.19 (3H, m), 1.93-1.99 (2H, m), 1.68-1.84 (4H, m), 1.55-1.70 (2H, m).
LC/MS RT=1.61; [M+H]+=360.39.

EXAMPLE 6

(S)-2-(5-Bromo-4-phenylpyrimidin-2-ylamino)-4H-1'-azaspiro[oxazole-5,3'-bicyclo[2.2.2]octane]1'-oxide

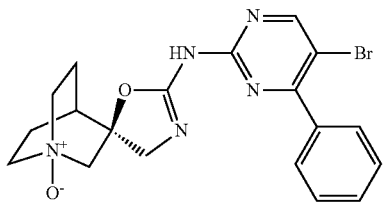 [SMILES: [O-][N+]12CCC(CC1)[C@]1(CN=C(Nc3ncc(Br)c(-c4ccccc4)n3)O1)C2]

mCPBA (0.060 g, 0.266 mmol) was added to a suspension of (R)—N-(5-bromo-4-phenylpyrimidin-2-yl)-4H-1'-azaspiro[oxazole-5,3'-bicyclo[2.2.2]octan]-2-amine (0.1 g, 0.241 mmol) in THF (10 ml). The mixture was stirred at room temperature for 18 h, concentrated, and purified by silica gel chromatography (5-25% 9:1 methanol:ammonium hydroxide-ethyl acetate) to afford (S)-2-(5-bromo-4-phenylpyrimidin-2-ylamino)-4H-1'-azaspiro[oxazole-5,3'-bicyclo[2.2.2]octane]1'-oxide as an off-white solid (0.066 g, 0.149 mmol, 62%). $^1$H NMR (400 MHz, MeOD) δ ppm 8.72 (1H, s), 7.74 (2H, dd, J=6.92, 2.64 Hz), 7.39-7.53 (3H, m), 4.01 (1H, d, J=10.58 Hz), 3.85 (1H, d, J=10.32 Hz), 3.61-3.74 (2H, m), 3.37-3.50 (3H, m), 3.19-3.26 (1H, m), 2.37-2.51 (1H, m), 2.26-2.33 (1H, m), 1.95-2.20 (3H, m). LC/MS RT=1.78; [M+2]+=432.19.

EXAMPLE 7

(S)-2-(5-Chloro-4-methylpyridin-2-yl)-4H-1'-azaspiro[oxazole-5,3'-bicyclo[2.2.2]octane]1'-oxide

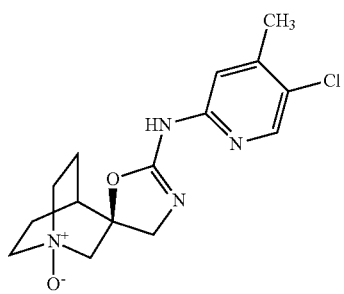 [SMILES: Cc1cc(NC2=NC[C@@]3(C[N+]4([O-])CCC3CC4)O2)ncc1Cl]

To (R)—N-(5-Chloro-4-methylpyridin-2-yl)-4H-1'-azaspiro[oxazole-5,3'-bicyclo[2.2.2]octan]-2-amine (0.04 g, 0.13 mmol) in THF (10 mL) was added m-CPBA (0.025 g, 0.14 mmol). The reaction stirred at room temperature for 2 hours and was then concentrated to a crude powder. The product was purified by chromatography (Biotage: 85% CHCl$_3$, 14% MeOH, 1% NH$_4$OH) to yield (S)-2-(5-chloro-4-methylpyridin-2-ylamino)-4H-1'-azaspiro[oxazole-5,3'-bicyclo[2.2.2]octane]1'-oxide (0.019 g, 0.06 mmol, 44% yield) as a white powder. $^1$H NMR (500 MHz, MeOD) δ ppm 8.18 (s, 1H), 6.75-7.09 (m, 1H), 4.00 (d, J=10.4 Hz, 1H), 3.84 (d, J=10.4 Hz, 1H), 3.61-3.78 (m, 2H), 3.41-3.54 (m, 3H), 3.23-3.38 (m, 3H), 2.45 (br. s., 1H), 2.25-2.38 (m, 4H), 1.88-2.22 (m, 1H). MS (LC/MS) R.T.=0.91; [M+H]+=323.11.

EXAMPLE 8

(S)-2-(5-Chloropyrazin-2-ylamino)-4H-1'-azaspiro[oxazole-5,3'-bicyclo[2.2.2]octane]1'-oxide

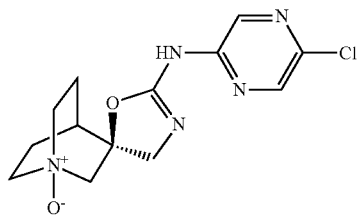 [SMILES: [O-][N+]12CCC(CC1)[C@]1(CN=C(Nc3cnc(Cl)cn3)O1)C2]

3-Chlorobenzoperoxoic acid (104 mg, 0.466 mmol) was added to a solution of (R)—N-(5-chloropyrazin-2-yl)-4H-1'-azaspiro[oxazole-5,3'-bicyclo[2.2.2]octan]-2-amine (114 mg, 0.388 mmol) in THF (3 mL) at room temperature and stirred for 2 h. The mixture was concentrated and the crude product was purified by flash chromatography on a 40 g silica gel cartridge with 10 to 30% [9:1 MeOH/NH4OH] in EtOAc, 30 min. Pure fractions were pooled, concentrated and dried.

The residue was dissolved in EtOAC/MeOH 95:5, passed thru a 0.22 micron filter, concentrated and dried under high vacuum to yield (S)-2-(5-chloropyrazin-2-ylamino)-4H-1'-azaspiro[oxazole-5,3'-bicyclo[2.2.2]octane]1'-oxide (113 mg, 94% yield).

$^1$H NMR (400 MHz, MeOD) δppm 8.25 (1H, d, J=1.51 Hz), 8.00 (1H, br. s.), 4.00 (1H, d, J=10.58 Hz), 3.85 (1H, d, J=10.58 Hz), 3.60-3.76 (2H, m), 3.35-3.52 (3H, m), 3.21-3.27 (1H, m), 2.34-2.52 (1H, m), 2.26-2.36 (1H, m), 2.00-2.21 (3H, m)

$^1$H NMR (400 MHz, ACETONITRILE-d$_3$) δ ppm 8.74 (1H, br. s.), 8.18 (1H, d, J=1.51 Hz), 8.01 (1H, br. s.), 3.89 (1H, d, J=10.32 Hz), 3.72 (1H, d, J=10.32 Hz), 3.50 (2H, q, J=14.52 Hz), 3.20-3.32 (3H, m), 3.03-3.15 (1H, m), 2.21-2.33 (1H, m), 2.18 (1H, br. s.), 1.95-2.05 (2H, m)

LCMS: RT=0.76 min, MH$^+$=310.0
[Waters Acquity: 2 to 98% B, 1 min gradient; hold 98% B, 0.5 min; flow rate 0.8 mL/min; Solvent A: 100% H2O/0.05% TFA; Solvent B: 100% ACN/0.05% TFA.]
HPLC: RT=4.67 min, Purity=100%
[XTERRA S3.5 C18 (4.6×150 mm): 5 to 100% B, 15 min gradient; flow rate 1 mL/min; Solvent A: 10 mM NH4OAc, pH6.8, in Water/ACN (95/5); Solvent B: 10 mM NH4OAc, pH6.8, in Water/ACN (5/95); 220/254 nM.]
HPLC: RT=7.26 min, Purity=99.6%
[Gemini S5 C18 (4.6×150 mm): 5 to 100% B, 15 min gradient, hold 100% B 3 min; flow rate 1 mL/min; Solvent A: 10 mM Ammonium Bicarbonate. pH 9.5, in Water/MeOH (95:5); Solvent B: 10 mM Amm. Bicarbonate. pH 9.5, in Water/MeOH (5:95); 220/254 nM].

EXAMPLE 9

(S)-2-(6-(1H-imidazol-1-yl)pyrimidin-4-ylamino)-4H-1'-azaspiro[oxazole-5,3'-bicyclo[2.2.2]octane]1'-oxide

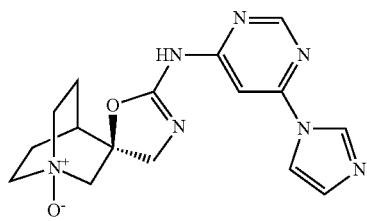

A solution of (R)—N-(6-(1H-imidazol-1-yl)pyrimidin-4-yl)-4H-1'-azaspiro[oxazole-5,3'-bicyclo[2.2.2]octan]-2-amine (52.9 mg, 0.163 mmol) and 3-chlorobenzoperoxoic acid (33.7 mg, 0.195 mmol) in 2 mL THF was stirred at room temperature for 24 h. The reaction was concentrated and the crude product was purified by flash chromatography on a 40 g silica gel cartridge with 20 to 40% [9:1 MeOH/NH4OH] in EtOAc, 40 min. Pure fractions were pooled, concentrated, and dried. The residue was dissolved in CDCl$_3$, filtered through a 0.4μ filter, concentrated, and dried under high vacuum to yield (S)-2-(6-(1H-imidazol-1-yl)pyrimidin-4-ylamino)-4H-1'-azaspiro[oxazole-5,3'-bicyclo[2.2.2]octane]1'-oxide (53 mg, 95% yield).

$^1$H NMR (400 MHz, MeOD) δ ppm 8.69 (1H, s), 8.60 (1H, d, J=1.01 Hz), 7.91 (1H, t, J=1.39 Hz), 7.15 (1H, d, J=0.76 Hz), 6.99 (1H, br. s.), 4.07 (1H, d, J=10.58 Hz), 3.92 (1H, d, J=10.58 Hz), 3.61-3.79 (2H, m), 3.36-3.53 (3H, m), 3.21-3.26 (1H, m), 2.30-2.48 (2H, m), 1.97-2.22 (3H, m)

LCMS: RT=1.23 min, MH$^-$=340.2, MH$^+$=342.1 [Phenomenex LUNA C18 3μ (2.0×30 mm); 0 to 100% B, 2 min gradient; flow rate 1 mL/min; Solvent A: 5% MeOH: 95% water: 10 mM NH4OAc; Solvent B: 95% MeOH: 5% water: 10 mM NH4OAc; 220 nM]
HPLC
RT=5.48 min, Purity=99.7%, Column: XbridgeC18 3.5 um, 3.0×150 mm
RT=6.74 min, Purity=98.9%, Column: Xbridge Phenyl 3.5 um, 3.0×150 mm
Method:
10-100% B, 15 min, 0.5 ml/min; 220/254 nM
Solvent Pair=10 mM amm. bicarb (pH=9.5)/water/methanol
Solvent A=10 mM amm. bicarb (pH=9.5)/95% water/5% methanol
Solvent B=10 mM amm. bicarb (pH=9.5)/5% water/95% methanol

EXAMPLE 10

(S)-2-(5-Phenylthiazol-2-ylamino)-4H-1'-azaspiro[oxazole-5,3'-bicyclo[2.2.2]octane]1'-oxide

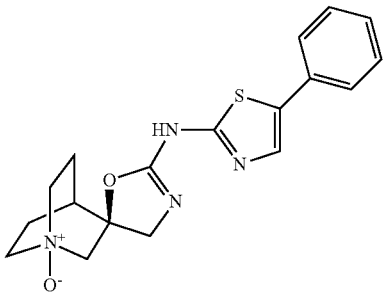 [SMILES: [O-][N+]12CCC(CC1)[C@]1(CN=C(Nc3ncc(-c4ccccc4)s3)O1)C2]

(R)—N-(5-Phenylthiazol-2-yl)-4H-1'-azaspiro[oxazole-5,3'-bicyclo[2.2.2]octan]-2-amine (0.101 g, 0.297 mmol) was dissolved in THF (15 mL) and treated with m-CPBA (0.061 g, 0.356 mmol) for 30 min. at room temperature. The reaction was concentrated in vacuo to afford the crude product. The crude product was purified by reverse phase HPLC to yield pure fractions. The fractions were concentrated via vacuo and dried in a vac. oven for 18 hours to yield (S)-2-(5-phenylthiazol-2-ylamino)-4H-1'-azaspiro[oxazole-5,3'-bicyclo[2.2.2]octane]1'-oxide (0.03 g, 0.082 mmol, 27.8% yield) as a white powder. $^1$H NMR (500 MHz, DMSO-d$_6$) δ ppm 7.86-8.12 (m, 1H), 7.64 (br. s., 2H), 7.44 (s, 3H), 4.13-4.31 (m, 3H), 3.97-4.07 (m, 1H), 3.90 (d, J=10.7 Hz, 4H), 3.54-3.74 (m, 1H), 2.28-2.42 (m, 1H), 1.95-2.24 (m, 3H). LC/MS: retention time 1.04 (M+1=357.1).

EXAMPLE 11

(S)-2-(6-Fluoro-3,4'-bipyridin-2'-ylamino)-4H-1'-azaspiro[oxazole-5,3'-bicyclo[2.2.2]octane]1'-oxide

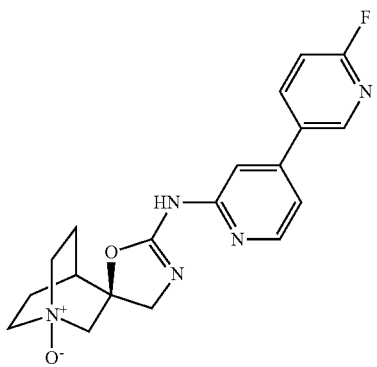 [SMILES: [O-][N+]12CCC(CC1)[C@]1(CN=C(Nc3cc(-c4ccc(F)nc4)ccn3)O1)C2]

(R)—N-(6-Fluoro-3,4'-bipyridin-2'-yl)-4H-1'-azaspiro[oxazole-5,3'-bicyclo[2.2.2]octan]-2-amine (0.11 g, 0.311 mmol) in THF (10 mL) was treated with m-CPBA (0.059 g, 0.342 mmol) and stirred at room temperature for 2 hours. Reaction was complete by TLC and the product was purified by chromatography (Biotage: 5-20% of 8:2 MeOH:NH$_4$OH in CHCl$_3$) and the pure fractions were combined to yield (S)-2-(6-fluoro-3,4'-bipyridin-2'-ylamino)-4H-1'-azaspiro[oxazole-5,3'-bicyclo[2.2.2]octane]1'-oxide (0.05 g, 0.134 mmol, 43.1% yield) as a yellow powder. $^1$H NMR (500 MHz, DMSO-d$_6$) δ ppm 9.11 (br. s., 1H), 8.64 (br. s., 1H), 8.21-8.43 (m, 2H), 7.04-7.44 (m, 3H), 3.77 (d, J=10.1 Hz, 2H), 2.98-3.65 (m, 6H), 2.18 (br. s., 2H), 1.74-2.01 (m, 3H). LC/MS: retention time 0.78 (M+1=370.2).

EXAMPLE 12

(S)-2-(1-Fluoroisoquinolin-3-ylamino)-4H-1'-azaspiro[oxazole-5,3'-bicyclo[2.2.2]octane]1'-oxide

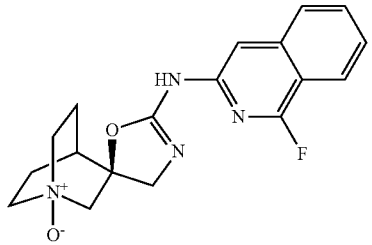 [SMILES: [O-][N+]12CCC(CC1)[C@]1(CN=C(Nc3cc4ccccc4c(F)n3)O1)C2]

To (R)—N-(1-Fluoroisoquinolin-3-yl)-4H-1'-azaspiro[oxazole-5,3'-bicyclo[2.2.2]octan]-2-amine (0.063 g, 0.193 mmol) in CHCl$_3$ (15 mL) was added m-CPBA (0.034 g, 0.195 mmol) at room temperature. The reaction was stirred at room temperature for 3 hours. TLC showed lower spot and no starting material. The mixture was purified by chromatography (Biotage: 15-20% of 9:1 MeOH:NH$_4$OH in CHCl$_3$; ~1.1 L) to yield the pure fractions. The fractions were combined and the solvent was removed to yield (S)-2-(1-fluoroisoquinolin-3-ylamino)-4H-1'-azaspiro[oxazole-5,3'-bicyclo[2.2.2]octane]1'-oxide (0.050 g, 0.146 mmol, 76% yield) as a white powder. $^1$H NMR (500 MHz, DMSO-d$_6$) δ ppm 8.12-8.42 (m, 1H), 8.01 (d, J=8.2 Hz, 1H), 7.86 (br. s., 1H), 7.73 (br. s., 1H), 7.43-7.60 (m, 1H), 6.93-7.35 (m, 1H), 3.69-4.05 (m, 1H), 3.58 (br. s., 1H), 3.00-3.33 (m, 6H), 2.19 (br. s., 2H), 1.94 (d, J=10.1 Hz, 3H). LC/MS: retention time 1.78 (M+1=343.1).

EXAMPLE 13

(S)-2-(5-Bromo-6-fluoropyridin-2-ylamino)-4H-1'-azaspiro[oxazole-5,3'-bicyclo[2.2.2]octane]1'-oxide

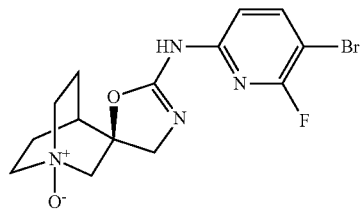 [SMILES: [O-][N+]12CCC(CC1)[C@]1(CN=C(Nc3ccc(Br)c(F)n3)O1)C2]

To (R)—N-(5-bromo-6-fluoropyridin-2-yl)-4H-1'-azaspiro[oxazole-5,3'-bicyclo[2.2.2]octan]-2-amine (0.064 g, 0.180 mmol) in CHCl$_3$ (15 mL) was added m-CPBA (0.032 g, 0.186 mmol) at room temperature. The reaction stirred at room temperature for 3 hours. TLC showed lower spot and no starting material. The mixture was purified by chromatography (Biotage: 15-20% of 9:1 MeOH:NH$_4$OH in CHCl$_3$; ~1.1 L) to yield the pure fractions. The fractions were combined and the solvent was removed to yield (S)-2-(5-bromo-6-fluoropyridin-2-ylamino)-4H-1'-azaspiro[oxazole-5,3'-bicyclo[2.2.2]octane]1'-oxide (0.045 g, 0.119 mmol, 65.9% yield) as a yellow powder. $^1$H NMR (500 MHz, DMSO-d$_6$) δ ppm 8.31-8.76 (m, 1H), 8.00 (br. s., 1H), 6.46-6.96 (m, 1H), 3.73 (d, J=11.0 Hz, 2H), 3.56 (br. s., 1H), 3.37 (br. s., 3H), 2.98-3.27 (m, 2H), 2.11 (br. s., 2H), 1.73-2.00 (m, 3H).
LC/MS: retention time 1.59 (M+1=372.95).

EXAMPLE 14

(S)-2-(5-Methyloxazolo[5,4-b]pyridin-2-ylamino)-4H-1'-azaspiro[oxazole-5,3'-bicyclo[2.2.2]octane]1'-oxide

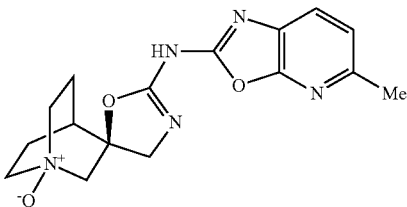

A 10 ml vial was charged with (3'R,4'S)—N-(5-methyloxazolo[5,4-b]pyridin-2-yl)-4H-1'-azaspiro[oxazole-5,3'-bicyclo[2.2.2]octan]-2-amine (40 mg, 0.13 mmol), m-chloroperoxybenzoic acid (34 mg, 0.15 mmol), and THF (640 µL) at ambient temperature. The resulting solution was stirred at ambient temperature for 1.5 h. The volatiles were then removed under reduced pressure and the crude reaction material was diluted with methanol and purified by silica-gel column chromatography (0-30% methanol ((containing 10% ammonium hydroxide)) in chloroform) to afford (S)-2-(5-methyloxazolo[5,4-b]pyridin-2-ylamino)-4H-1'-azaspiro[oxazole-5,3'-bicyclo[2.2.2]octane]1'-oxide (35 mg, 0.10 mmol, 78% yield) as a colorless oil. $^1$H NMR (400 MHz, MeOD) δ ppm 7.69-7.74 (1H, m), 7.14-7.19 (1H, m), 4.07-4.13 (1H, m), 3.92-3.98 (1H, m), 3.70-3.80 (2H, m), 3.42-3.54 (3H, m), 3.23-3.30 (1H, m), 2.55 (3H, s), 2.35-2.51 (2H, m), 2.00-2.25 (3H, m). MS (LC/MS) R.T.=1.32, [M+H]$^+$=330.49.

EXAMPLE 15

(S)-2-(6-Methylbenzo[d]oxazol-2-ylamino)-4H-1'-azaspiro[oxazole-5,3'-bicyclo[2.2.2]octane]1'-oxide

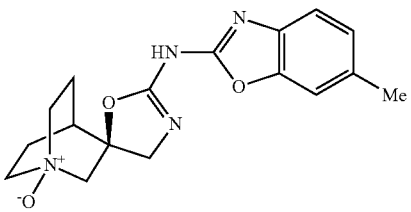

A 10 ml vial was charged with (3'R,4'S)—N-(6-methylbenzo[d]oxazol-2-yl)-4H-1'-azaspiro[oxazole-5,3'-bicyclo[2.2.2]octan]-2-amine (75 mg, 0.24 mmol), m-chloroperoxybenzoic acid (65 mg, 0.29 mmol), and THF (1.2 mL) at ambient temperature. The resulting solution was stirred at ambient temperature for 1.5 h. The volatiles were removed under reduced pressure and the crude reaction material was diluted with methanol and purified by silica-gel column chromatography (0-30% methanol ((containing 10% ammonium hydroxide)) in chloroform) to afford (S)-2-(6-methylbenzo[d]oxazol-2-ylamino)-4H-1'-azaspiro[oxazole-5,3'-bicyclo[2.2.2]octane]1'-oxide (76 mg, 0.23 mmol, 96% yield) as a colorless oil. $^1$H NMR (400 MHz, MeOD) δ ppm 7.31-7.35 (1H, m), 7.20-7.23 (1H, m), 7.03-7.08 (1H, m), 4.06-4.11 (1H, m), 3.91-3.96 (1H, m), 3.71-3.81 (2H, m), 3.44-3.55 (3H, m), 3.25-3.31 (1H, m), 2.35-2.51 (5H, m), 2.00-2.24 (3H, m). MS (LC/MS) R.T.=1.42, [M+H]$^+$=329.09.

EXAMPLE 16

(S)-2-(5-Methoxyoxazolo[5,4-b]pyridin-2-ylamino)-4H-1'-azaspiro[oxazole-5,3'-bicyclo[2.2.2]octane]1'-oxide

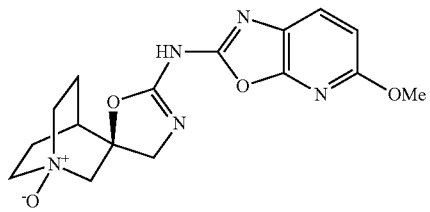

A 10 ml vial was charged with (3'R,4'S)—N-(5-methoxyoxazolo[5,4-b]pyridin-2-yl)-4H-1'-azaspiro[oxazole-5,3'-bicyclo[2.2.2]octan]-2-amine (75 mg, 0.23 mmol), m-chloroperoxybenzoic acid (61 mg, 0.27 mmol), and THF (1.1 mL) at ambient temperature. The resulting solution was stirred at ambient temperature for 1.5 h. The volatiles were removed under reduced pressure and the crude reaction material was diluted with methanol and purified by silica-gel column chromatography (0-30% methanol ((containing 10% ammonium hydroxide)) in chloroform) to afford (S)-2-(5-methoxyoxazolo[5,4-b]pyridin-2-ylamino)-4H-1'-azaspiro[oxazole-5,3'-bicyclo[2.2.2]octane]1'-oxide (33 mg, 0.095 mmol, 42% yield) as a white solid. $^1$H NMR (400 MHz, DMSO-d$_6$) δ ppm 9.07 (1H, br. s.), 7.78 (1H, d, J=8.3 Hz), 6.74 (1H, d, J=8.5 Hz), 3.82-3.96 (5H, m), 3.69 (1H, dd, J=14.2, 1.9 Hz), 3.48 (1H, d, J=14.1 Hz), 3.07-3.40 (4H, m), 2.10-2.30 (2H, m), 1.88-2.06 (3H, m). MS (LC/MS) R.T.=1.28, [M+H]$^+$=346.09.

BIOLOGICAL TESTING

The following section details the liquid chromatography with tandem mass spectrometry (LC/MS/MS)-based bioanalytical methods developed to support the analysis of the in vivo biological samples (brain, plasma, urine) from studies conducted in the dog and rat.

Standard Curve Preparation. Standard curves and quality control (QC) samples defining the dynamic range of the bioanalytical method were prepared in the respective biological matrix and processed in the same fashion as the test samples, unless otherwise noted.

Sample Preparation: Blood, Plasma, Serum, Urine. Plasma and blood samples were prepared as described below. If dilutions were required, an aliquot of the sample was diluted into the respective matrix. For the analysis of urine samples, an aliquot was first diluted into blank plasma and then treated as described below.

Sample preparation was conducted manually or on a Packard MultiPROBE automated liquid handler. The internal standard (IS) solution (1000 nM (S,E)-5-bromo-N-(1'-azaspiro[oxazolidine-5,3'-bicyclo[2.2.2]octane]-2-ylidene)pyrazin-2-amine) was prepared in acetonitrile. Two hundred microliters of the IS solution was added to each well of a Strata protein precipitation filter plate (Phenomenex, Torrance, Calif.). Biological samples (60 μL) were added to the filter plate. The filter plate was attached atop a standard 96 well plate and the entire unit was centrifuged at 1100 rpm for 2 minutes. The supernatant was collected in the 96 well plate. Five microliters of each sample was injected onto the LC/MS/MS system for analysis.

Instrumentation. The UHPLC system used was an Agilent 1200 series (Agilent Technologies, Wilmington, Del.) coupled with CTC Analytics HTS PAL Auto Sampler (Leap Technologies, Carrboro, N.C.) that was equipped with a cooling stack so that samples were maintained at 10° C. during analysis. The analytical column used was a Waters Acquity HSS T3 (2.1×50 mm, 1.8 um particles) at 60° C. The mobile phase, which consisted of 0.1% formic acid in water (A) and 0.1% formic acid in acetonitrile (B), was delivered at a flow rate of 0.6 mL/min. The analytical gradient conditions are listed in the following table.

TABLE I

Mobile Phase Gradient for Compound A and Compound B LC/MS/MS Analysis

| Time (min) | % A | % B | Flow Rate (mL/min) |
|---|---|---|---|
| 0.0 | 100 | 0 | 0.6 |
| 0.1 | 100 | 0 | 0.6 |
| 1.8 | 50 | 50 | 0.6 |
| 1.9 | 50 | 50 | 0.6 |
| 2.0 | 5 | 95 | 0.6 |
| 2.1 | 5 | 95 | 0.6 |
| 2.2 | 100 | 0 | 0.6 |
| 2.3 | 100 | 0 | 0.6 |

The retention times for Compound A, Compound B, and the internal standard occurred at 1.26, 1.29, and 1.26 min, respectively. The total analysis time was 2.3 min.

The UHPLC was interfaced to an API4000 QTrap LC/MS/MS System® (AppliedBiosystems/MDS Sciex, Foster City, Calif.) equipped with an electrospray ionization interface operating in the positive ionization mode. The source temperature was 500° C. Detection of each analyte was achieved through selected reaction monitoring. Ions representing the precursor (M+H)$^+$ species for Compound A, Compound B, and the IS were selected in quadrupole 1 and collisionally dissociated with nitrogen to generate specific product ions, which were subsequently monitored by quadrupole 3. The transitions monitored and the mass spectrometer settings are summarized in the following table.

TABLE II

Transitions Monitored and Mass Spectrometer Settings for LC/MS/MS Sample Analysis

| Compound | Precursor Ion | Product Ion | Declustering Potential | Collision Energy |
|---|---|---|---|---|
| Compound A | 309.1 | 171.1 | 70 | 37 |
| Compound B | 325.2 | 171.1 | 60 | 35 |
| IS | 338.3 | 122.2 | 80 | 45 |

Standard Curve Ranges. Unless otherwise specified, the analysis of Compound A and Compound B were conducted against a standard curve ranging from 0.6 to 1,250 nM and 4.8 to 5,000 nM, respectively. The standard curve was fitted with a linear regression weighted by the square of the reciprocal concentration ($1/x^2$). Standards were analyzed in duplicate. Quality control samples were prepared in blank biological matrix at concentration levels within the range of the standard curve. The predicted concentrations of more than 80% of the QCs from various different matrices were within 20% of nominal values, indicating acceptable assay performance.

Quantification of Compound A and Compound B by LC/MS

The following section details the liquid chromatography with mass spectrometry (LC/MS)-based bioanalytical methods developed to support the analysis of in vitro samples from hepatocyte and reaction phenotyping studies.

Instrumentation. Compound A was quantitated using an HPLC separation with mass spectrometric detection. The HPLC system consisted of Shimadzu LC-10ADvp pumps and a Shimadzu SIL-10ADvp autosampler linked to a Waters XBridge C18 5-micron (2.1×50 mm) HPLC column. Mobile phase A consisted of water containing 0.1% formic acid, while mobile phase B consisted of acetonitrile containing 0.1% formic acid. Chromatography was performed at an oven temperature of 45° C. with a flow rate of 0.3 mL/min. The HPLC gradient used is summarized in the following table.

TABLE III

Mobile Phase Gradient for Compound A and Compound B LC/MS Analysis

| Time (min) | % A | % B | Flow Rate (mL/min) |
|---|---|---|---|
| 0.0 | 95 | 5 | 0.3 |
| 1.0 | 95 | 5 | 0.3 |
| 3.2 | 0 | 100 | 0.3 |
| 3.3 | 0 | 100 | 0.3 |
| 4.2 | 0 | 100 | 0.3 |
| 4.3 | 95 | 5 | 0.3 |
| 5.0 | 95 | 5 | 0.3 |

The retention times for Compound A, Compound B, and the IS occurred at 2.85, 2.87, and 2.85 min, respectively. The total analysis time was 5.8 min.

The HPLC system was interfaced with a Waters Micromass LCQ mass spectrometer equipped with an electrospray source. Compound A was detected as its [M+H]+ ion (m/z 309) using positive-ion electrospray ionization. Compound B was detected as its [M+H]+ ion (m/z 325) using positive-ion electrospray ionization. The source block temperature was 130° C., the desolvation temperature was 350° C., the capillary voltage was 3 kV, and the cone voltage was 29V for Compound A and 39V for Compound B. Ultra-high purity nitrogen was used as desolvation gas at 350 L/h. Peak areas of the m/z 309 product ion of Compound A were measured against the peak areas of the IS. Results of the analysis were expressed as peak area ratios, Peak Area (Compound A)/Peak Area (IS).

Conversion of Compound B to Compound A In Vivo

Conversion of N-oxide, Compound B, to Compound A in the rat. The conversion of Compound B to Compound A was evaluated in male Sprague-Dawley rats (260-280 g) Animals (N=3 per group) received Compound B as an intra-duodenal infusion (10 mg/kg over 10 minutes) via an indwelling intra-duodenal cannula (IDC) with collection via the intra-portal vein. Serial blood samples were obtained predose and at 0.17, 0.25, 0.5, 0.75, 1, 2, 4, 6, 8, and 24 hours post dose. Plasma samples, obtained by centrifugation at 4° C. (1500-2000×g), were stored at −20° C. until analysis.

All conversion studies in rats were performed in animals containing indwelling cannulas in the duodenum and portal vein. The studies were designed to isolate the role of the GI tract in the reduction of Compound B. Table IV summarizes the exposure of Compound B and Compound A in the portal vein following an intra-duodenal infusion of Compound B in the rat. After intra-duodenal infusion of Compound B, concentrations of Compound A increased in samples obtained from the portal vein ($AUC_{Compound\ A}/AUC_{Compound\ B}=3.6$) indicating reduction of the N-oxide to the parent drug in vivo.

TABLE IV

| Time (hours) | Compound A (uM) | Compound B (uM) |
|---|---|---|
| 0.167 | 0.003 | 0.601 |
| 0.25 | 0.007 | 0.758 |
| 0.5 | 0.112 | 0.177 |
| 0.75 | 0.207 | 0.090 |
| 1 | 0.448 | 0.069 |
| 2 | 0.75 | 0.052 |
| 4 | 0.455 | 0.018 |
| 6 | 0.434 | < LLQ |
| 8 | 0.125 | < LLQ |
| 24 | 0.006 | < LLQ |

"LLQ" = "lower limit of quantitation"

Table V summarizes the PK parameters of Compound B and the appearance of Compound A following a single dose in rats.

TABLE V

| Species/Strain: | Rat/Sprague-Dawley | |
|---|---|---|
| Gender/Number of animals: | Male/3 per timepoint | |
| Feeding condition: | Fasted/non-treated | |
| Vehicle/Formulation: | PEG-400/water(80:20)/Solution | |
| Method of administration: | IDC infusion (10 minute)/PVC collection | |
| Sample: | Plasma | |
| Assay: | LC/MS/MS | |
| Route: | Intra-Duodenal | |
| Dose of Compound B (mg/kg): | 10 | |
| Analytes: | Compound B | Compound A |
| Cmax (μM) | 0.76 ± 0.24 | 0.86 ± 0.34 |
| AUC(0-4) (μM · h) | 0.34 ± 0.04 | 1.22 ± 1.10 |
| AUC(0-24 h) (μM · h) |  | 2.55 ± 1.93 |

Conversion of N-oxide, Compound B, to Compound A in the dog. The conversion of Compound B to Compound A was evaluated in a crossover-design study in male beagle dogs. Three animals (5 to 8 kg) received Compound B by IV infusion (1 mg/kg over 5 minutes) via a cephalic vein and by oral gavage (5 mg/kg), with a 1-week washout between treatments. Serial blood samples (~0.3 mL) were collected from a saphenous vein predose and at (0.083, 0.17 IV only), 0.25, 0.5, 0.75, 1, 2, 4, 6, 8, and 24 hours post dose, followed by centrifugation at 4° C. (1500-2000×g) to obtain plasma. Samples were stored at −20° C. until analysis by LC/MS/MS.

Table VI summarizes the PK parameters of Compound B and the appearance of Compound A following a single dose in dogs. Following either an IV or PO dose, the conversion of Compound B to Compound A was observed; however, it was more extensive after oral dosing. After PO dosing of Compound B (10 mg/kg), the plasma AUC of Compound A was 0.7 μM·h. This represents roughly 40% of the oral AUC of Compound A observed following PO administration of Compound A alone (1.74 μM·h). After IV dosing of Compound B, the plasma AUC of Compound A was only 0.03 μM·h. This represents about only 3% of the AUC of Compound A observed following IV administration of Compound A. These results demonstrate that conversion of Compound B to Compound A occurs in vivo.

TABLE VI

| Species/Strain: | Beagle dog | | Beagle dog | |
|---|---|---|---|---|
| Gender/Number of animals: | Male/3 per timepoint | | Male/3 per timepoint | |
| Feeding condition: | Fed | | Fasted | |
| Vehicle/Formulation: | PEG-400/water(80:20)/ Solution | | PEG-400/0.01NHCl(80:20)/ Solution | |
| Method of administration: | IV infusion (5 minute) | | Oral gavage | |
| Sample: | Plasma | | Plasma | |
| Assay: | LC/MS/MS | | LC/MS/MS | |
| Route: | IV | | Oral | |
| Dose of compound B (mg/kg): | 1 | | 5 | |
| Analytes: | Compound B | Compound A | Compound B | Compound A |
| Cmax (μM) | | | 0.85 ± 0.46 | |
| AUC(0-24 h) (μM · h) | 3.84 ± 0.92 | 0.03 ± 0.01 | 5.16 ± 0.68 | 0.70 ± 0.20 |
| AUC(INF) (μM · h) | 3.94 ± 1.01 | | 5.69 ± 0.39 | |
| CLTp (mL/min/kg) | 13.7 ± 4.0 | | | |
| Vss (L/kg) | 2.0 ± 0.2 | | | |
| T-HALF (h) | 9.4 ± 6.5 | | | |
| Bioavailability (%) | | | 27 ± 15 | |

It is thus demonstrated in two species that administration of the prodrug, Compound B, results in the appearance of the active ligand, Compound A.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The invention claimed is:
1. A compound of the formula

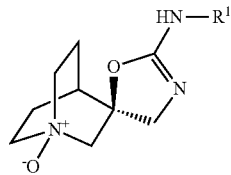

wherein:
$R^1$ is selected from the group consisting of isoxazolyl, pyrazolyl, oxazolyl, thiazolyl, imidazolyl, oxadiazolyl, thiadiazolyl, triazolyl, pyridinyl, pyrazinyl, pyridazinyl, pyrimidinyl, triazinyl, quinolinyl, isoquinolinyl, tetrahydroisoquinolinyl, quinoxalinyl, quinazolinyl, naphthyridinyl, indazolyl, indolyl, 2-indolonyl, benzisoxazolyl, benzoisothiazolyl, benzoxazolyl, benzotriazolyl, benzimidazolyl, furopyridinyl, thienopyridinyl, thienopyrimidinyl, isothiazolopyridinyl, thiazolopyridinyl, thiazolopyridinonyl, thiazolopyrazinyl, thiazolopyrimidinyl, triazolopyridinyl, triazolopyrazinyl, pyrrolotriazinyl, 5,6-dihydrobenzo[h]quinazolinyl, 5H-chromeno[4,3-d]pyrimidinyl, 6,7-dihydro-5H-cyclopenta[d]pyrimidinyl, 5,6,7,8-tetrahydroquinazolinyl, 7,8-dihydroquinazolin-5(6H)-onyl, tetrahydrobenzothiazolyl, imidazothiazolyl, oxazolopyridinyl, triazolopyridazinyl, triazolopyrimidinyl, imidazolopyridazinyl, imidazopyrazinyl, imidazopyridinyl, pyrrolopyrazinyl, benzotriazolyl, pyrrolopyrimidinyl, purinyl, pyrrolopyridinyl, and benzotriazinyl and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, nitro, $C_{1-4}$alkylsulfonyl, $NR^2R^3$, pyrrolidinonyl, methylenedioxy, furyl, thienyl, pyrazolyl, imidazolyl, pyrrolyl, oxadiazolyl, thiazolyl, triazolyl, pyrazinyl, pyrimidinyl, naphthyl, $C_{1-4}$alkylamido, $CONR^2R^3$, pyridyl, phenyl, and benzyl, and where imidazolyl, pyridyl, phenyl, pyrrolyl, oxadiazolyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, phenyl, benzyl, pyridylmethyl and $NR^2R^3$;
$R^2$ is hydrogen, phenyl, $C_{1-4}$alkyl, $C_{1-4}$hydroxyalkyl, or $C_{1-4}$aminoalkyl;
$R^3$ is hydrogen, $C_{1-4}$alkyl, $C_{1-4}$hydroxyalkyl, or $C_{1-4}$aminoalkyl;
or $R_2$ and $R_3$ taken together with the nitrogen atom to which they are attached is azetidinyl, pyrrolidinyl, piperidinyl, piperazinyl, N—($C_{1-4}$alkyl)piperazinyl, morpholinyl, or homopiperidinyl;
or a pharmaceutically acceptable salt thereof.

2. A compound of claim 1 where $R^1$ is thiazolyl, pyridinyl, pyrazinyl, pyrimidinyl, isoquinolinyl, or quinoxalinyl, and is substituted with 0-2 substituents selected from the group consisting of halo; alkyl; alkoxy; cycloalkoxy; pyrazolyl; imidazolyl; pyridinyl substituted with 0-2 halo, alkyl, or alkoxy substituents; and phenyl substituted with 0-2 halo, alkyl, or alkoxy substituents; or a pharmaceutically acceptable salt thereof.

3. A compound of claim 2 where $R^1$ is (phenyl)thiazolyl, (fluoro)(bromo)pyridinyl, (chloro)(methyl)pyridinyl, chloropyrazinyl, (fluoropyridinyl)pyridinyl, (bromo)(phenyl)pyrimidinyl, (cyclopentoxy)pyrimidinyl, (imidazolyl)pyrimidinyl, ((methyl)phenyl)pyrimidinyl, isoquinolinyl, fluoroisoquinolinyl, or quinoxalinyl, or a pharmaceutically acceptable salt thereof.

4. A compound of claim 2 where $R^1$ is bromopyridinyl, dichloropyridinyl, (pyridinyl)pyridinyl, (pyrazolyl)pyrimidinyl, methoxypyrimidinyl, (methoxypyridinyl)pyrimidinyl, (phenyl)pyrimidinyl, or bromomchloropyrazinyl, or a pharmaceutically acceptable salt thereof.

5. A compound of claim 1 selected from the group consisting of

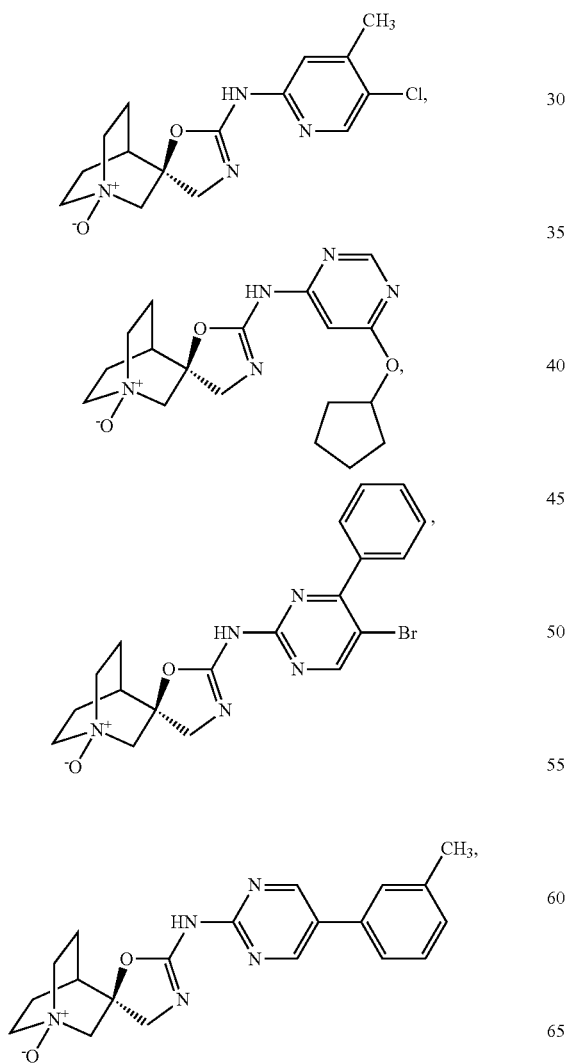

-continued

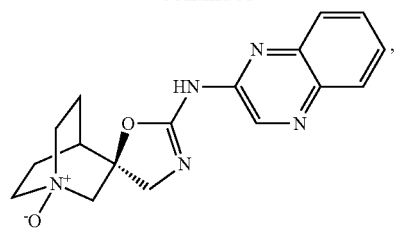

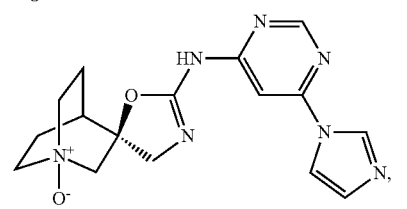

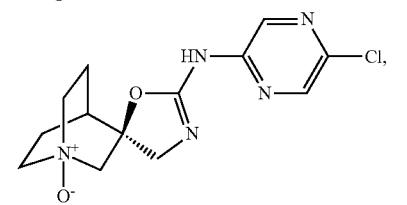

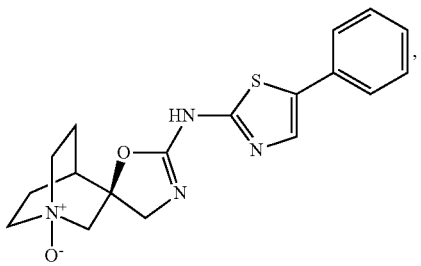

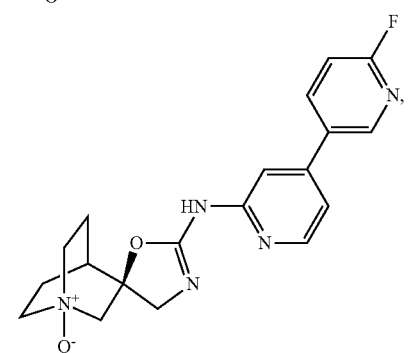

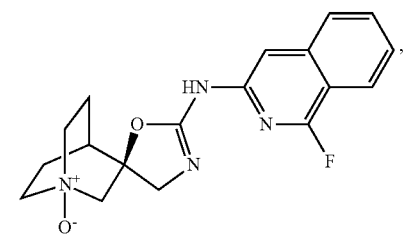

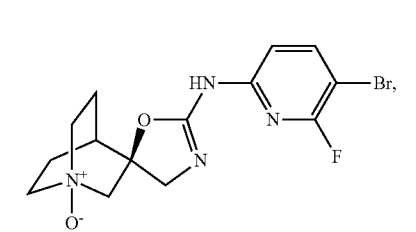

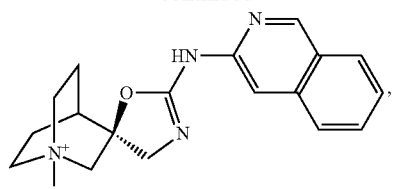
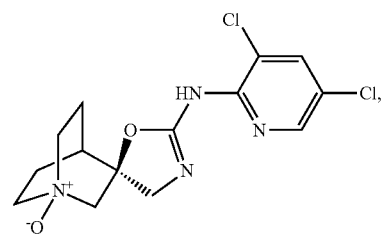
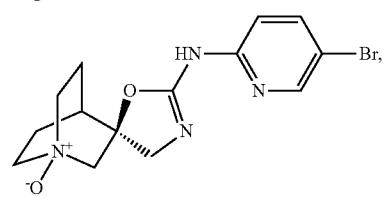
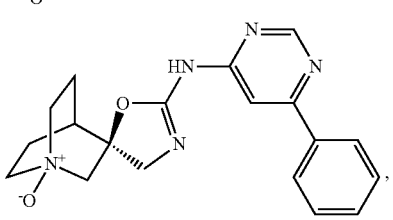
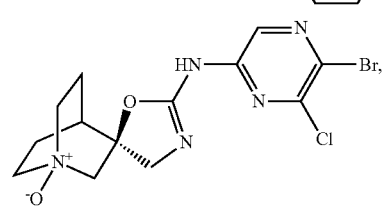
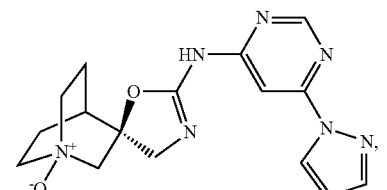
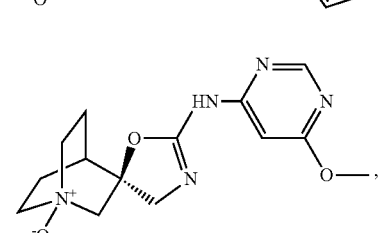
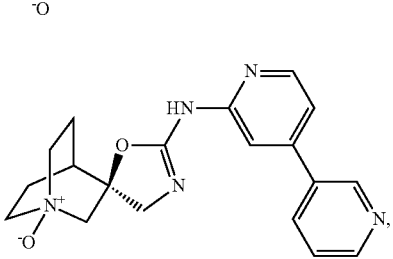
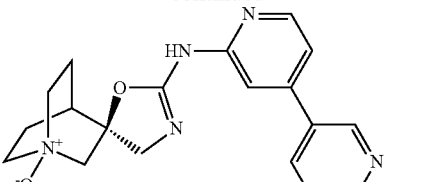
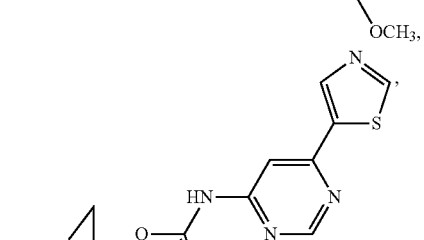
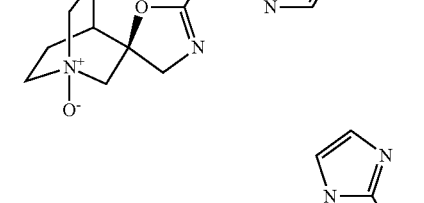
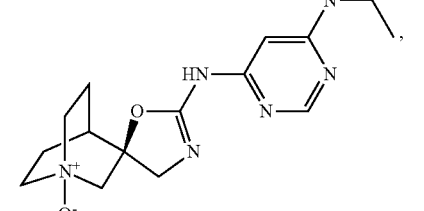
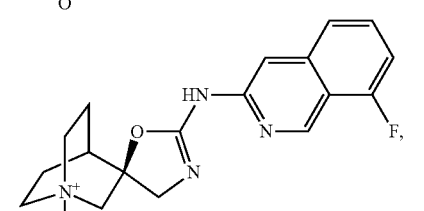
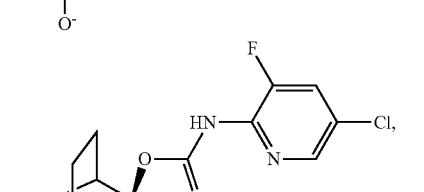
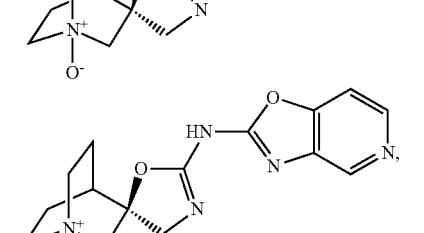
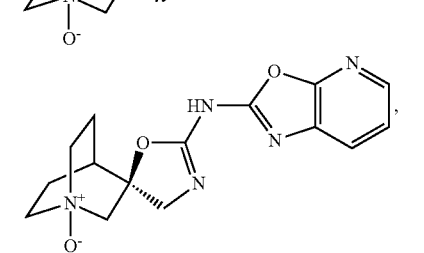

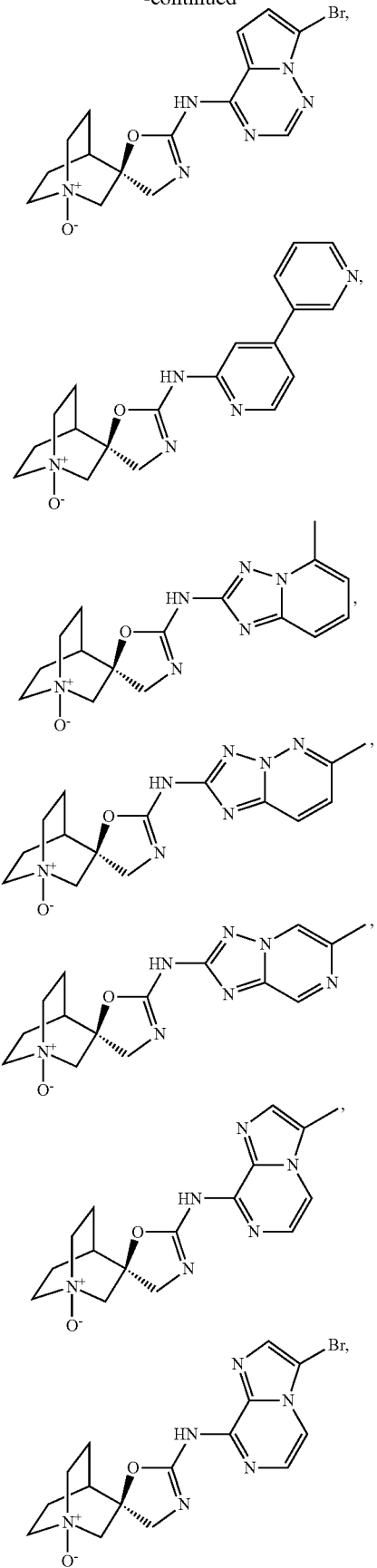
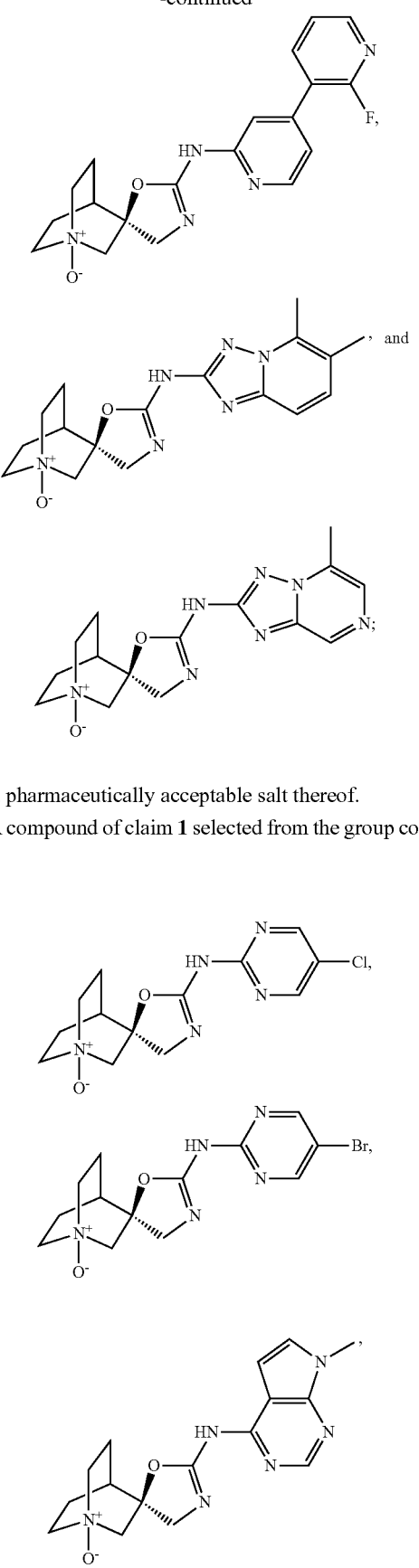
or a pharmaceutically acceptable salt thereof.
6. A compound of claim 1 selected from the group consisting of -continued

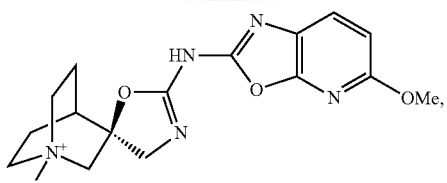

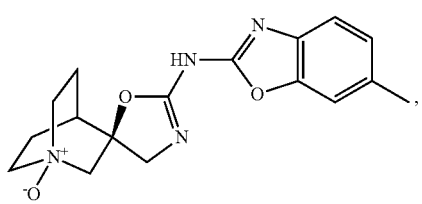

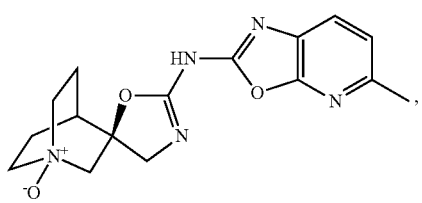

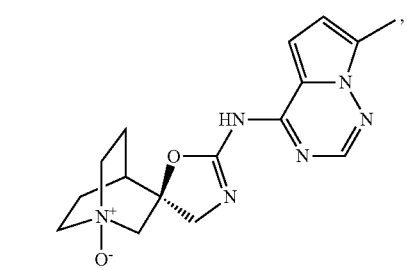

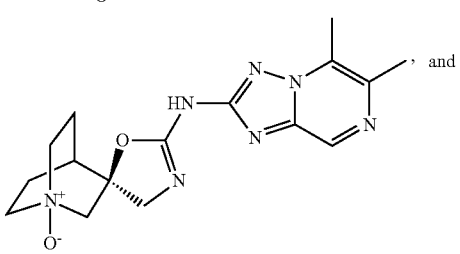

-continued

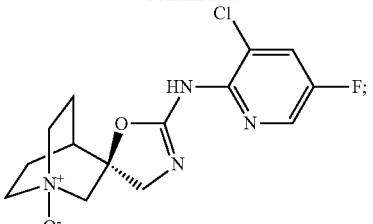

or a pharmaceutically acceptable salt thereof.
7. The compound of claim 1

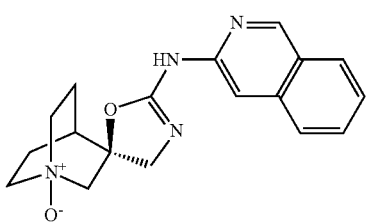 [SMILES: [O-][N+]12CCC(CC1)[C@]1(CN=C(Nc3cc4ccccc4cn3)O1)C2]

or a pharmaceutically acceptable salt thereof.
8. The compound of claim 1

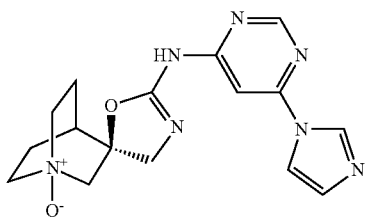 [SMILES: [O-][N+]12CCC(CC1)[C@]1(CN=C(Nc3cc(-n4ccnc4)ncn3)O1)C2]

or a pharmaceutically acceptable salt thereof.
9. A pharmaceutical composition comprising a therapeutically effective amount of a compound of claim 1, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 8,481,555 B2  
APPLICATION NO. : 13/097153  
DATED : July 9, 2013  
INVENTOR(S) : Kimberley A. Lentz et al.

Page 1 of 1

It is certified that error appears in the above-identified patent and that said Letters Patent is hereby corrected as shown below:

In the Claims:

Claim 1:

Column 26, line 8, change "benzotriazolyl," to -- benzothiazolyl, --.

Column 26, line 63, change "$R_2$ and $R_3$" to -- $R^2$ and $R^3$ --.

Claim 4:

Column 27, line 20, change "bromomchloropyrazinyl," to -- bromochloropyrazinyl, --.

Claim 5:

Column 30, first structure, change

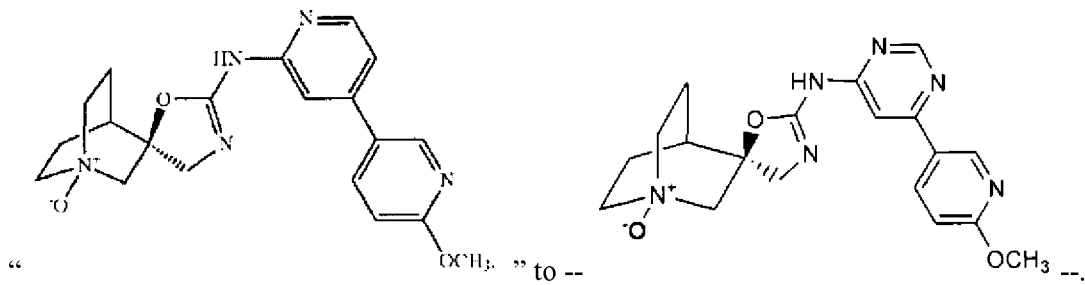

Signed and Sealed this
Twenty-ninth Day of April, 2014

Michelle K. Lee
*Deputy Director of the United States Patent and Trademark Office*